United States Patent [19]

Pidgeon

[11] Patent Number: 4,931,498
[45] Date of Patent: Jun. 5, 1990

[54] IMMOBILIZED ARTIFICIAL MEMBRANES

[75] Inventor: Charles Pidgeon, West Lafayette, Ind.

[73] Assignee: Purdue Research Foundation, West Lafayette, Ind.

[21] Appl. No.: 160,196

[22] Filed: Feb. 25, 1988

[51] Int. Cl.$^5$ .................... A61K 37/02; C08G 283/00; C08L 89/00
[52] U.S. Cl. ................................. 525/54.1; 530/345; 530/811; 530/812; 530/813; 530/814; 530/815; 210/656; 210/927; 428/402; 428/403; 428/406; 428/407
[58] Field of Search ............... 530/345, 811, 812, 813, 530/814, 815; 428/357, 402, 403, 406, 407; 210/656, 927; 525/54.1

[56] References Cited

U.S. PATENT DOCUMENTS

| | | | |
|---|---|---|---|
| Re. 30,125 | 10/1979 | Li et al. | 210/22 R |
| 3,917,527 | 11/1975 | Shaltiel | 210/31 C |
| 4,014,785 | 3/1977 | Li et al. | 210/22 D |
| 4,155,844 | 5/1979 | Li et al. | 210/22 R |
| 4,292,181 | 9/1981 | Li et al. | 210/638 |
| 4,348,329 | 9/1982 | Chapman | 260/403 |
| 4,569,794 | 2/1986 | Smith et al. | 530/344 |
| 4,703,004 | 10/1987 | Hopp et al. | 435/68 |

OTHER PUBLICATIONS

"Affinity Surfactants as Reversibly Bound Ligands for High-Performance Affinity Chromatography", J. L. Torres, R. Guzman, R. G. Carbonell, and P. K. Kilpatrick, *Analytical Biochemistry*, vol. 171, pp. 411–418 (1988).

"Expression of Human Insulin-Like Growth Factor I in Bacteria: Use of Optimized Gene Fusion Vectors to Facilitate Protein Purification", *Biochemistry*, 1987, vol. 26, pp. 5239–5244, Moks, T. et al.

"Synthesis and Characterization of an Amphiphilic Peptide that Undergoes a pH Triggered Random Coil—a-Helical Transition", *Biophysical Journal*, vol. 49, 1986, p. 134a, Subbarao, N., et al.

"Phospholipid Polymers—Synthesis and Spectral Characteristics", *Biochimica et Biophysica Acta.*, vol. 602 (1980), pp. 57–69, Johnston, D. S., et al.

"Polymerization of Mono- and Bi-Functional Diacetylene Derivatives in Monolayers at the Gas–Water Interface", Day, D., et al., *Chem. Abstracts*, vol. 92, 1980, pp. 181701.

"Polymer-Supported Membranes", *Macromolecules*, 1984, vol. 17, pp. 1292–1293, Albrecht, O., et al.

"Further Evidence for Polymer-Supported Membranes and a Statement Concerning Synthetic Scope and Surface Structure", *Macromolecules*, vol. 17, pp. 1293–1294, Regen, S. L., et al.

"On the Formation and Structure of Self-Assembling Monolayers", Gun, J., et al., *Journal of Colloid and*

(List continued on next page.)

Primary Examiner—John Kight, III
Assistant Examiner—Nathan M. Nutter
Attorney, Agent, or Firm—Barnes & Thornburg

[57] ABSTRACT

Methods and materials are described for the preparation of novel immobilized membrane compositions. The described compositions are useful for evaluating membrane association charcteristics of chemical compounds, and as a chromatographic support material for separation/purification of biomolecules and particularly those expressed by genetically transformed cells as novel hybrid proteins having covalently bound membrane-binding peptides. Novel phospholipid carboxylates are useful intermediates for the preparation of chromatography supports having surfaces formed as covalently bound artificial membranes which simulate natural cellular membranes. The immobilized membrane compositions are adapted for use in chromatographic systems to study interactions of biologically active substances with membranes in vitro. The immobilized membranes are expected to find use for vaccine production, protein purification, chiral separations/synthesis, as a combination reverse phase/normal phase HPLC support material, and for drug screening.

57 Claims, 6 Drawing Sheets

OTHER PUBLICATIONS

*Interface Science*, vol. 101, No. 1, Sep. 1984, pp. 201-213.

"Oriented Ultrathin Membranes from Monomeric and Polymeric Amphiphiles: Monolayers, Liposomes and Multilayers", Ringsdorf, H., et al., *Thin Solid Films*, vol. 152 (1987), pp. 207-222.

"Potential of Membrane-Mimetic Polymers in Membrane Technology", Fendler, J., *Journal of Membrane Science*, vol. 30 (1987), pp. 323-346.

"Investigations of Polymerizable Multilayers as Gas Separation Membranes", Albrecht O., et al., *Journal of Membrane Science*, vol. 22 (1985), pp. 187-197.

"On the Formation and Structure of Self-Assembling Monolayers", Maoz, R., et al., *Journal of Colloid and Interface Science*, vol. 100, No. 2, Aug. 1984, pp. 465-496.

"Molecular-Level Control Over Surface Order in Self-Assembled Monolayer Films of Thiols on Gold", Bain, C. D. et al., *Science*, Apr. 1, 1988, pp. 62-63.

"Self-Assembling Surfaces", Williams, R. J. P., *Nature*, vol. 332, Mar. 31, 1988, p. 393.

"Ionic Recogniation and Selective Response in Self-Assembling Monolayer Membranes on Electrodes", Rubinstein, I., et al., *Nature*, vol. 332, Mar. 31, 1988, pp. 426-429.

"Surfactant Vesicles as Membrane Mimetic Agents: Characterization and Utilization", Fendler, J. H., *Acc. Chem. Res.*, vol. 13, 1980, pp. 7-13.

"Retention Behavior of Homologous Series in Reversed-Phase Liquid Chromatography Using Micellar, Hydro-Organic and Hybrid Mobile Phases", *Anal. Chem.*, 1987, vol. 59, pp. 2738-2747, Khaledi, M. G., et al.

"Direct Serum Injection with Micellar Liquid Chromatography: Chromatographic Behavior and Recovery of Cephalosporins", *Anal. Chem.*, 1987, vol. 59, pp. 2732-2734, Haginaka, J., et al.

"The Separation of Proteins by Reversed-Phase High-Performance Liquid Chromatography", Hancock, W. S. et al., *High Performance Liquid Chromatography*, vol. 3 (1983), Academic Press, Inc., pp. 49-85.

"Separation of Peptides on Chemically Bonded Reversed Phases", Hearn, M., *High Performance Liquid Chromatography*, vol. 3, (1983) Academic Press, Inc., pp. 95-112.

*Immobilized Cells and Organelles*, ed. Bo Mattiasson, CRC Press, Boca Raton, Fla. (1983), vols. 1 and 2, Chapters by mattiason, Gestrelius, and Ochoa.

"Anti-Sense Peptide Recognition of Sense Peptides: Direct Quantitative Characterization with the Ribonuclease S-Peptide System Using Analytical High-Performance Affinity Chromatography", *Biochemistry*, vol. 26, 1987, pp. 669-675, Shai, Y., et al.

"The Role of Protein Structure in Chromatogrpahic Behavoir", Regnier, F. E., *Science*, vol. 238, Oct. 16, 1987, pp. 319-323.

"Column Liquid Chromatography of Integral Membrane Proteins", Welling, G. et al., *Journal of Chromatography*, vol. 418 (1987), pp. 223-243.

"A Method for Determination of Saturated Phosphatidylcholine", by Tadashi Shimojo, Masao Abe and Masaru Phta, *Journal of Lipid Research*, vol. 15, 1974, pp. 525-527.

"Rapid Purification of Phospholipase $A_2$ from *Crotalus Adamanteus* Venom by Affinity Chromatography", by Charles O. Rock and Fred Snyder, *The Journal of Biological Chemistry*, vol. 250, Aug. 25, 1975, pp. 6564-6566.

"Functionalized Silica Gel as a Support for Solid-Phase Organic Synthesis", by John F. Keana, Masato Shimizu and Karen K. Jernstedt, *The Journal of Organic Chemistry*, vol. 51, No. 10, May 16, 1986, pp. 1641-1644.

"Production of Glycolipid Affinity Matrices by Use of Heterobifunctional Crosslinking Agents", by Clifford A. Lingwood, *Journal of Lipid Research*, vol. 25, 1984, pp. 1010-1013.

"Synthesis of Phospholipids Suitable for Covalent Binding to Surfaces", by R. Krishnamohanrao Kallury, Ulrich J. Krull and Michael Thompson, *J. Org. Chem.*, 1987, vol. 52, pp. 5478-5480.

"Spontaneous Assembly of Phospholipid Monolayers Via Adsorption onto Gold", by Tadeusz Diem, Bogdan Czajka, Bruce Weber and Steven L. Regen, *J. Am. Chem. Soc.*, 1986, vol. 108, pp. 6094-6095.

"Organized Monolayers by Adsorption III. Irreversible Adsorption and Memory Effects in Skeletonized Silane Monolayers", by Jacob Sagiv, *Israel Journal of Chemistry*, vol. 18, 1979, pp. 346-353.

"Organized Self-Assembling Monolayers on Electrodes Part I. Octadecyl Derivatives on Gold", by E. Sabatina, Israel Rubenstein, Rivka Maoz and Jacob Sagiv, *J. Electroanal. Chem.*, vol. 219 (1987), pp. 365-371.

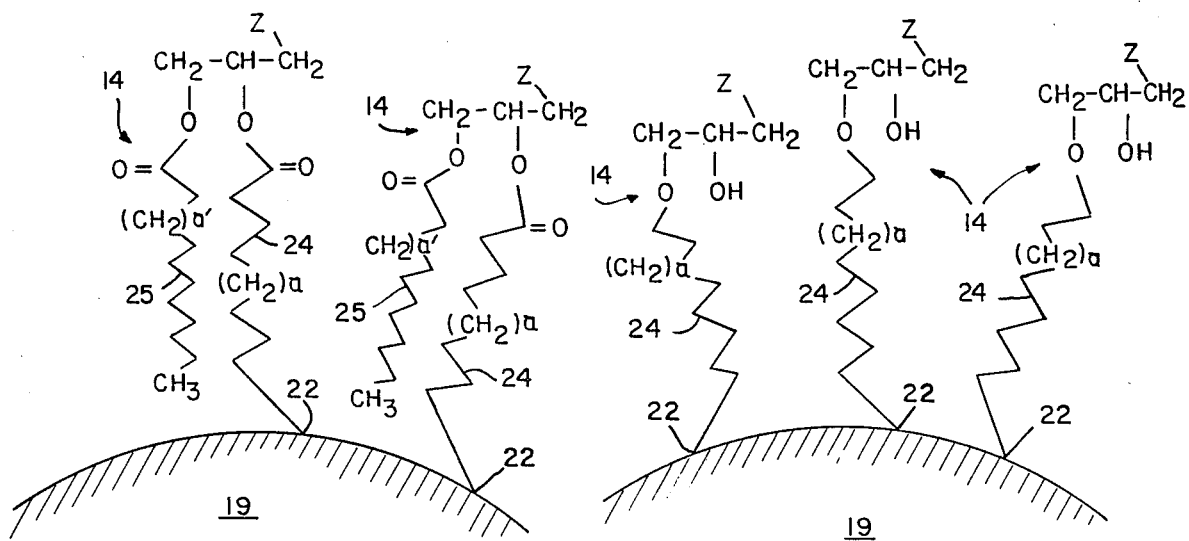
FIG. 4          FIG. 5
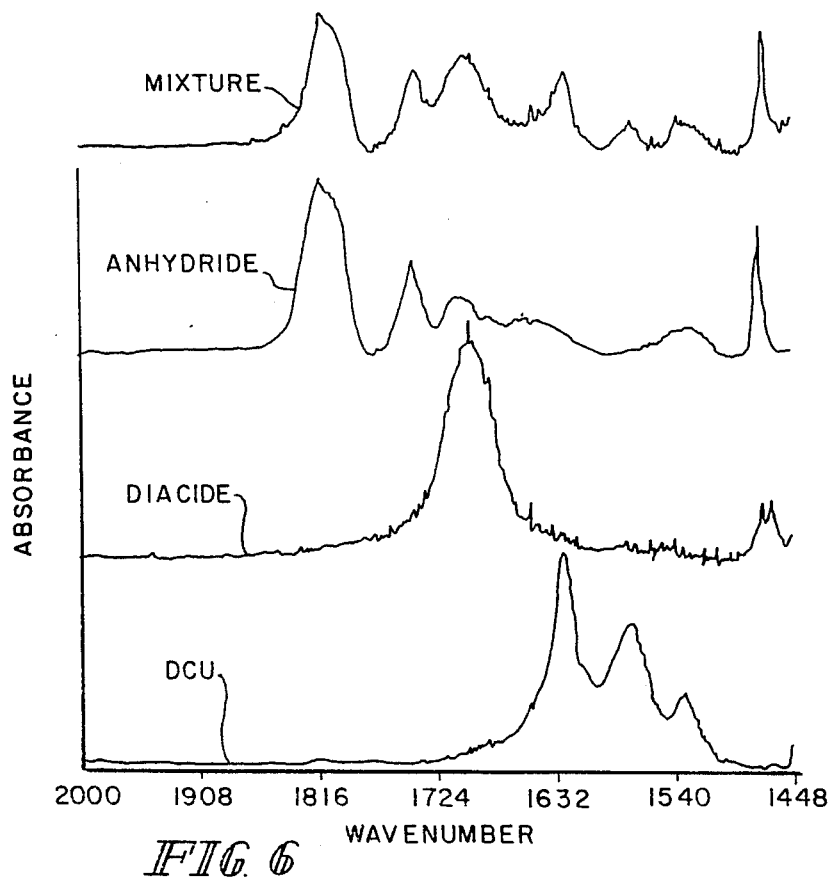
FIG. 6

IMMOBILIZED ARTIFICIAL MEMBRANES

This invention relates to novel chromatography supports uniquely adapted for the study and purification of biologically active compounds. More particularly, this invention relates to the use of amphiphilic constituents of biological membranes as the stationary phase in chromatographic systems. Membrane constituents are immobilized on the surface of commercially available chromatography support materials to form artificial membranes designed to mimic the associative characteristics of natural biological membranes. Used in chromatography systems, particularly high pressure liquid chromatography (HPLC), the support materials of this invention provide a powerful tool for isolation of chemical substances and identification of new drug leads.

Background and Summary of the Invention

With the rapid growth of research and development in the field of biotechnology there has been an ever increasing demand for new methods and materials critical to the efficient performance of biotechnology research. Indeed, whole new industries have evolved to support the biotechnology revolution. One technology area that has received much attention in service of the needs of the biotech industry is that of chromatographic systems. The separation and purification of biomolecules is of paramount importance, not only to the molecular biologist performing preliminary cloning experiments, but also to the biochemical engineer responsible for the commercial production of high purity products. Much emphasis has been placed on the adaptation of traditional chromatography techniques and systems to meet the many special purification problems of the biotechnology industry. The literature is replete with disclosures of chromatographic theories, techniques and materials for separation of purification of biomolecules.

Types of chromatography which have been applied to the purification of biomolecules, that is, molecules derived from biological sources, include size exclusion chromatography, ion exchange chromatography, bioaffinity chromatography, reversed-phase chromatography and hydrophobic interaction chromatography, among others. The application and efficiency of each of those types of chromatography procedures relies on the selectivity of surface-surface interactions between the solute molecules and the stationary phase of the chromatography system, each interacting with the mobile liquid phase. A wide variety of stationary phase chromatography support materials are commercially available.

The present invention is directed to a new stationary phase chromatographic support material, the surface of which is designed to mimic the structure and surface-surface interactivity of biological cell membranes. Consequently, separation of biomolecules in chromatographic systems utilizing the immobilized artificial membrane supports of the present invention are the result of molecular interactions similar to the interactions of said biomolecules and biological membranes in vivo. More specifically, use of the present supports allow separation of a wide variety of peptides/proteins using an aqueous mobile phase without (or with minimum use of) the added protein-denaturing solvents commonly used in the now popular reversed-phase chromatographic systems. Many peptides can be separated in the same undenatured form they have when they interact with cell membranes in vivo.

The present compositions having covalently bound artificial membrane structure can be employed in chromatographic systems using a highly polar or non-polar mobile phase.

The immobilized artificial membrane-bearing chromatographic supports of this invention also find application to a novel generic protein purification procedure for hybrid proteins expressed by genetically engineered microorganisms. A biologically active protein is expressed as a hybrid protein covalently linked to a membrane-binding peptide through a selectively cleavable peptide linkage. The hybrid peptide is first purified using an immobilized membrane chromatographic support in accordance with this invention, and thereafter, the hybrid peptide is subjected to predetermined conditions for selective cleavage at a cleavage site between the active protein and the membrane binding peptide.

Possibly more significant than use of the present chromatographic supports as a tool for separation and purification of biomolecules is the potential offered by use of the present supports in a high performance chromatographic system for studying the interaction between solute molecules in the mobile phase and an immobilized membrane-excipient stationary phase which can include receptors, enzymes, antibodies and the like. Thus, the present chromatographic supports can serve as a powerful tool for the evaluation and study of drug-membrane/membrane excipient interactions, and they can find use as an in vitro indicator of potential or probable drug activity. Moreover, the artificial membrane bearing supports of the present invention can be used for catalysis reactions and chiral syntheses known to take place in biological or artificial membrane (liposome) environments. The present supports will also find use for vaccine preparation in that it will allow isolation and purification of membrane-binding fractions of viral homogenates.

In accordance with the present invention a composition of matter is provided which comprises a mechanically stable particulate support structure dimensioned for use in a chromatographic system, an artificial membrane structure on the surface of said support material and a means for immobilizing the membrane structure on said surface. The membrane structure comprises an amphiphilic compound having a hydrophilic headgroup portion and a hydrophobic portion. The molecules of the amphiphilic compound collectively define the membrane structure on the surface of the support material so that the membrane structure, in the preferred embodiment, has a hydrophobic inner portion and a hydrophilic outer headgroup portion.

"Immobilized" as used to describe the membrane structure on the surface of the present chromatographic supports is to be regarded as relative to the mobile phase. Thus while the molecules of the amphiphilic compound can be covalently bonded for "immobilization", they can also be "immobilized" relative to a hydrophilic polar (aqueous) liquid phase by hydrophobic interaction between the hydrophobic portion of said amphiphilic compounds and a hydrophobic surface on the particulate support structure. The preferred amphiphilic compounds forming the immobilized membrane structure are those occurring in artificial membranes (liposomes) and biological cell membranes. Phospholipids are most preferred. The immobilized membrane structures can be modified by adsorption of other biological membrane constituents, such as lipids, including phospholipids other than that used as the principal membrane-forming phospholipid, peptides/proteins, saccharides and the like.

Preparation of preferred covalently immobilized membrane chromatographic supports in accordance with this invention can be accomplished utilizing a novel phospholipid carboxylates derived by reaction of $C_{10}$–$C_{16}$ cyclic dicarboxylic acid anhydrides with glycero-phosphatides and lysophospholipids.

BRIEF DESCRIPTION OF THE DRAWINGS

FIG. 4 and FIG. 5 are partial cross-sectional views of chromatography support particles of this invention having covalently bound phospholipids and lysophospholipids respectively.

FIG. 6 illustrates infrared absorbance spectra for several intermediate compounds and a mixture thereof.

DETAILED DESCRIPTION OF THE INVENTION

In accordance with the present invention a chromatography support material is prepared to have a surface designed to mimic the structural and physico-chemical characteristics of natural biological membranes.

Biological membranes elicit affinity for virtually every type of biomolecule. All solutes in biological fluids/systems, including drugs, sugars, lipids, nucleic acids, amino acids, peptides and proteins interact with biological cell membranes. Indeed, such interactions between biomolecules and cell membranes are fundamental to cell function and viability. The chromatography supports in accordance with this invention take advantage of the selective interaction of biomolecules with biological membranes; they are designed to have an immobilized amphiphilic surface structure which resembles that of biological membranes.

Figure 1:
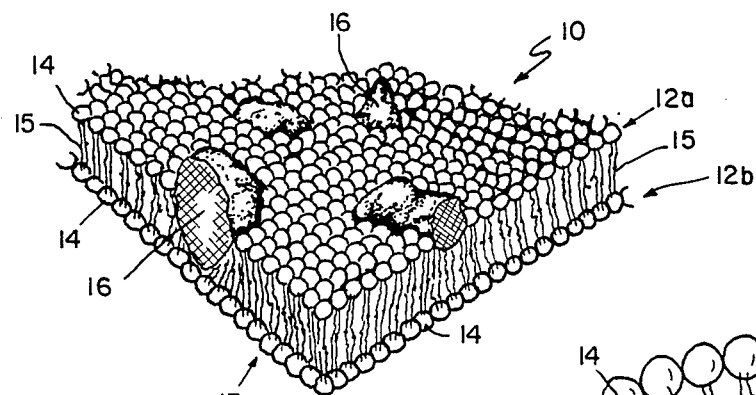
FIG. 1 illustrates the structure of biological membranes.

There are many illustrations in the literature of membrane structure and the arrangement of membrane constituents. One such illustration is shown in FIG. 1. It is the so-called fluid mosaic model for membrane structure originally proposed by Singer and Nicholson in Science, 175, 720, 1972, and later adapted by Hancock and Sparrow in *High Performance Liquid Chromatography*, Vo. 3, Academic Press 1983 at page 51. The biological membrane structure 10 is shown as a bi-layer 12(a), 12(b) of amphiphilic phospholipid molecules 13, each having a headgroup portion 14 and a hydrophobic portion 15. The headgroup portions 14 of the respective bi-layer phospholipids collectively define outer hydrophilic membrane surfaces separated by a non-polar (hydrophobic) environment defined by the hydrophobic portions 15 of the predominant phospholipid constituents of the membrane structure. In addition to the amphiphilic phospholipid molecules 13, biological membranes have other constituents 16 present, including, for example, membrane-associated proteins, such as receptor molecules, enzymes, and the like critical for regulation of cell function and other constituents such as lipids (cholesterol, for example) and saccharides.

In accordance with this invention there is provided a novel composition of matter comprising a mechanically stable particulate structure dimensioned for use in a chromatographic system, an artificial membrane structure on the surface of the support material and means for immobilizing said membrane structure on the surface of the support material. The membrane structure comprises an amphiphilic compound having a hydrophilic headgroup portion and a hydrophobic portion, said amphiphilic compound selected from phospholipids and other biological membrane constituents. The immobilized membrane structure is formed to have, like biological membranes, an outer hydrophilic headgroup portion and an inner non-polar (hydrophobic) portion.

Immobilization of the membrane structure can be accomplished either by covalent bonding of the component amphiphilic molecules, by hydrophobic interaction of the amphiphilic molecules with a hydrophobic surface on the particulate support structure or by a combination of hydrophobic interaction and covalent bonding. Each method of membrane immobilization offers some advantage and the preferred method can be determined after consideration of the intended application of the immobilized membrane support material. Thus, while covalent bonding of the constituent amphiphilic compounds forming the membrane structure will likely provide a more stable (i.e, more resistance to "mobilization" of component molecules) immobilized membrane structure and one usable with a wide range of mobile phases, amphiphilic molecules covalently bound to the support surface to collectively define the immobilized membrane structure do not have the lateral mobility of amphiphilic molecules in biological membranes. On the other hand, artificial membrane structures immobilized solely by the hydrophobic interaction of the membrane forming amphiphilic with a hydrophobic surface on a particulate support will have the lateral mobility such molecules inherently have in biological membranes. Use of hydrophobic interaction as a means for immobilizing the artificial membrane structure suffers from the disadvantage of reduced chromatography support life and mobile phase restrictions. Thus, an immobilized membrane support prepared by contacting a membrane-forming solution of a phospholipid such as phosphatidylcholine with, for example, a commercially available reversed-phase chromatographic support material will be limited to use with polar mobile phases which do not interfere with the hydrophobic interaction of the immobilization of the artificial membrane structure. Further, even where the mobile phase is limited to water, one can expect that the phospholipids, due to their amphiphilic character and the character of solute molecules in the mobile phase, will be leached slowly from the "hydrophobic interaction immobilized" membrane structure. Regeneration of such hydrophobic interaction immobilized membrane supports can be accomplished, for example, by perfusing a fresh solution of the phospholipid through a chromatographic column containing the membrane-bearing support material.

Immobilized membrane supports can also be prepared making use of both hydrophobic interaction and covalent bonding. For example, a hydrophobic reversed-phase particulate support material can be used as a base for forming an immobilized membrane from phospholipids having cross-linkable functional groups on the hydrophobic portion of the phospholipid molecules. Exemplary of such phospholipids are those described by Chapman in U.S. Pat. No. 4,348,329, issued Sept. 7, 1982, the disclosure of which is expressly incorporated herein by reference. The phospholipids disclosed by Chapman have in the hydrophobic portion a $C_8$–$C_{26}$ fatty acid ester having a conjugated di-yne functionality that can be crosslinked by actinic radiation with like groups to give intermolecular and intramolecular crosslinking. Thus such conjugated di-yne phospholipids can be brought into contact in solution with hydrOphobiC reversed-phase particles or a resinous (polymeric) particulate support material having a hydrophobic surface, to form a membrane-like phospholipid monolayer on the particle surface which thereafter can be exposed to radiation and thereby crosslinked to form a membrane-like pellicular coating effectively immobilized by covalent bonding on the particle surface.

Alternatively, phospholipids having reactive functional groups on their hydrophobic portion can be used to form the artificial membrane structure and thereafter, or in conjunction with membrane formation, they can be reacted with functional groups bound to the surface of the particulate support to covalently bond all or a substantial portion of the amphiphilic molecules constituting the immobilized membrane structure to the surface of the support.

The nature of such covalent bonding is not critical to function of the immobilized artificial membrane supports in accordance with this invention. Thus, covalent bonding of amphiphilic molecules bearing reactive functional groups to support surfaces through, or by reaction with, surface functional groups can be accomplished by a radiation-induced crosslinking reaction or, for example, by nucleophilic or condensation-type reactions resulting in formation of ester, ether, or amide bonds, for example.

It will be recognized that the immobilized artificial membrane-bearing supports prepared in accordance with this invention can be formed from single amphiphilic compounds or from mixtures of different amphiphilic compounds, if necessary, to modify the surface characteristics of the immobilized membrane-bearing chromatography support materials.

The mechanically stable particulate support structures used as a foundation for the present immobilized membrane structures are well known in the art. They can be porous or non-porous and formed of silica, alumina, titania or of resins having sufficient structural integrity to withstand the pressures found in high performance chromatography systems. Particle size can range from about 5 to about 100 microns, more preferably from about 5 to about 50 microns in diameter. Commercially available $C_8$ and $C_{18}$ reversed-phase particulate supports are conveniently used to form immobilized membrane supports in accordance with this invention wherein the membranes are immobilized through hydrophobic interaction of the hydrophobic surface of said supports and the hydrophobic portion of applied amphiphilic compounds. Other commercially available particulate supports can be used advantageously to form covalently immobilized membrane supports. Thus, for example in a preferred embodiment of this invention, Nucleosil-300(7NH$_2$), a silica based support having a particle size of about 7 microns and bearing covalently bound propylamine groups can be used as described in more detail hereinbelow to provide an immobilized membrane bearing chromatography support wherein the amphiphilic phospholipid molecules constituting the membrane structure are each covalently bound to the particle surface. Again, the nature of the covalent linkage is not critical to the function of the immobilized membrane supports in accordance with this invention.

Other commercially available particulate support structures having functional groups capable of reacting with and forming covalent bonds with functional groups on the hydrophobic portions of amphiphilic phospholipid compounds can be predictably employed. Thus, for example, commercially available pellicular coated chromatography support materials having available functional groups for forming covalent bonds with amphiphilic compounds are acceptable for use as mechanically stable support structures. More particularly, supports having a pellicular coating formed form a polyamine, such as polyethyleneimine, crosslinked with an epoxy resin or other amine crosslinking agents are suitable support structures for the present compositions. Such supports are described by Regnier et al. in U.S. Pat. No. 4,245,005, issued Jan. 13, 1981.

Figure 2A:
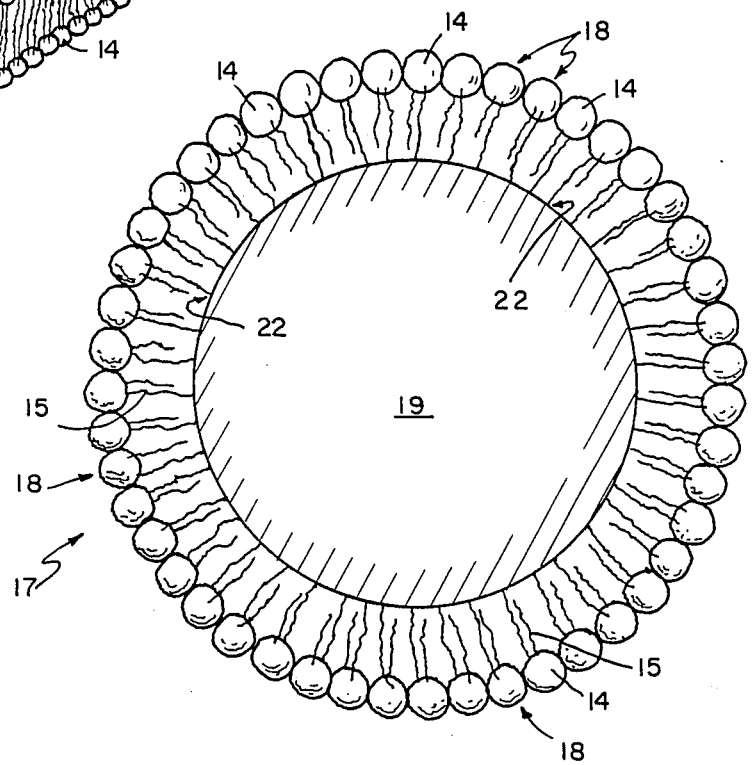
FIGS. 2(a) and 2(b) are cross-sectional views of chromatography support particles of the invention.
Figure 3A:
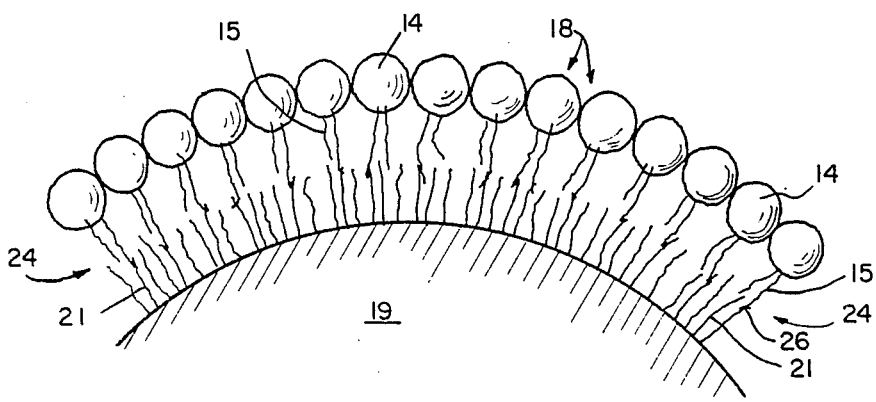
FIGS. 3(a) and 3(b) are partial cross-sectional views of chromatography support particles of the invention.
Figure 2:
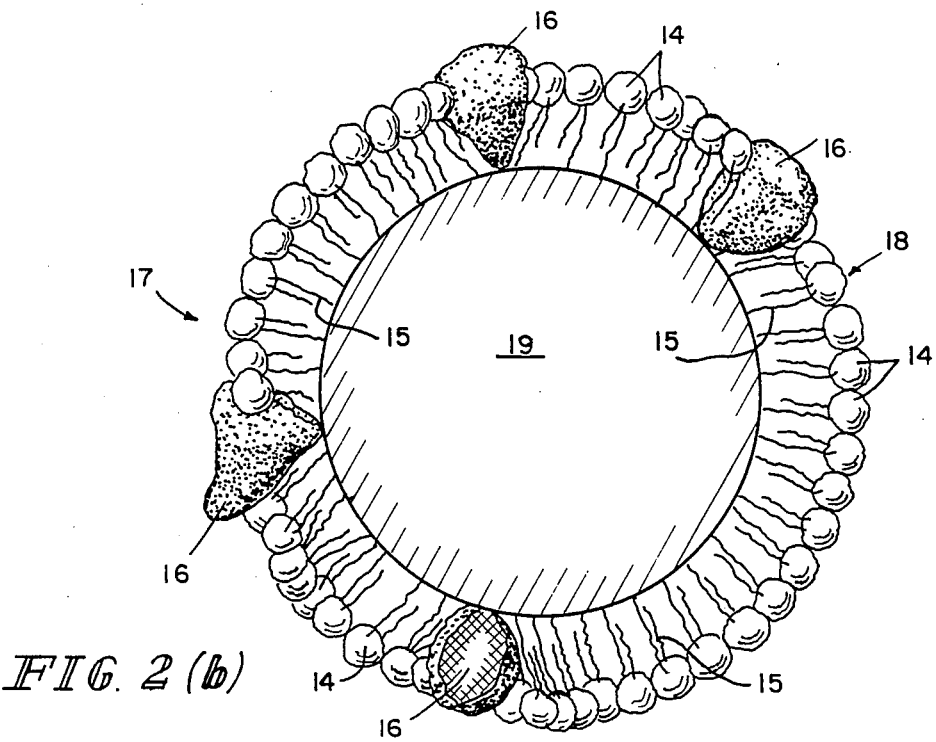
Figure 3:
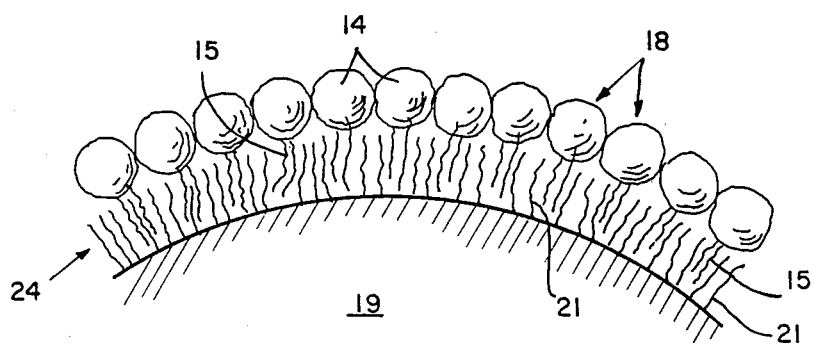

FIGS. 2 and 3 illustrate immobilized membrane-bearing particulate chromatography supports in accordance with this invention. With reference to FIG. 2(a) the immobilized membrane structure comprises covalently bound amphiphilic molecules 18 having a hydrophilic headgroup portion 14 and a hydrophobic portion 15. The molecules of amphiphilic compounds are covalently bonded through a linkage 22 to the surface of a mechanically stable particulate support 19. The immobilized membrane structure can be viewed practically as one-half of the bi-layer 12(a), 12(b) of the biological membrane 10 illustrated in FIG. 1, although supports having a bi-layer-like surface are also completed by this invention. The membrane structure presents an outer hydrophilic surface, i.e., the hydrophilic headgroups 14, and a hydrophobic inner portion collectively defined by the hydrophobic portions 15 of the covalently bound amphiphilic molecules 18.

FIGS. 3(a) and (b) illustrate an immobilized membrane structure 24 comprised of a multiplicity of amphiphilic molecules 18, most preferably phospholipid molecules, having a headgroup portion 14 and a hydrophobic portion 15 on a particle 19 having a hydrophobic surface structure 21 and a locus of hydrophobic interaction 26 between the hydrophobic surface structure 21 and the hydrophobic portion 15 of the amphiphilic molecules 18 FIG. 3(b) likewise illustrates a hydrophilic interaction immobilized membrane structure 24 on the surface of a particle 19 having a hydrophobic surface structure 21. In FIG. 3(b), however, the membrane structure 24 is shown such that the hydrophobic portion 15 of the amphiphilic molecules 18 are interdigitated with hydrophobic substituents collectively defining the hydrophobic surface structure 21, resulting in an enhanced locus of hydrophobic interaction 26 and therefore an increased stability (resistance to mobilization) of the immobilized artificial membrane structure.

Preferred amphiphilic molecules used for forming the immobilized membranes in accordance with this invention are amphiphilic molecules found in natural biological membranes. Exemplary of such are lecithins, lysolecithins, cephalins, sphingomyelin, cardiolipin, glycolipids, gangliosides and cerebrosides. A preferred group of amphiphilic compounds adapted for use in accordance with this invention are phospholipids. Of those phospholipids, lecithins and lysolecithins are particularly preferred. Thus immobilized membranes in accordance with this invention can be formed on support materials utilizing phosphatidylcholine, phosphatidylethanolamine, N-methylphosphatidylethanolamine, N,N-dimethylphosphatidylethanolamine, phosphatidic acid, phosphatidylserine, phosphatidylinositol and phosphatidylglycerol. Phosphatidylcholine, the most predominant phospholipid in biological membranes, is particularly preferred. Such amphiphilic compounds can be used to form immobilized membranes directly on hydrophobic reversed-phase particulate supports to provide hydrophobic interaction immobilized membrane surfaces. Alternatively, those compositions can be modified chemically to have reactive functional groups at or near the terminus of the hydrophobic portion of those molecules, said functional groups being capable of forming covalent bonds with reactive functional groups on the surface of the support material.

The amount of phospholipid used to form the immobilized artificial membrane supports in accordance with this invention should be sufficient to cover the surface of the support structure at a concentration of about 1 to about 2 molecules of amphiphilic compound per 100 square Angstroms of surface area of the support structure. Where the amphiphilic compound is phosphatidylcholine covalently bound to the surface of the support it should be employed in an amount sufficient to cover the surface of the support structure at a concentration of about 1.3 to about 1.6 molecules per 100 square Angstroms of the support structure.

The immobilized artificial membrane structures in accordance with this invention can be prepared to contain, in addition to the above-described immobilized amphiphilic molecules, other biological membrane constituents, including but not limited to, lipids (including other phospholipids), peptides or proteins (including receptors, enzymes, antibodies and the like), saccharides, oligonucleotides, polynucleotides and membrane-binding analogues of peptides, saccharides, oligonucleotides and polynucleotides. "Membrane-binding analogues" as used herein refers to derivatives which have been chemically modified to bear at least one additional membrane-binding group which functions to increase the membrane-associative character of the derivatized compounds. Thus, for example, the membrane associative characteristics of a peptide or protein can be enhanced by covalently binding such compounds to another chemical entity known to have high affinity for biological membranes, for example, peptides having amino acid sequences corresponding to all or a functional portion of a known transmembrane peptide sequence or other membrane-binding molecules such as cholesterol or cholesterol esters. Membrane-binding sequences can be identified empirically in a chromatography system utilizing a support of this invention such as that shown in FIG. 2(a). High retention times on such a system are indicative of high membrane affinity.

An immobilized membrane such as that shown in FIG. 2(a) can be treated with a solution of one or more membrane constituents having greater affinity toward the immobilized membrane structure than for its solution solvent molecules so that the membrane constituent will be adsorbed or absorbed onto or into the immobilized membrane structure. The product of such treatment is illustrated in FIG. 2(b) to show the adsorption/absorption of such membrane constituents 16 within the immobilized membrane structure on the particle surface Such added membrane constituents can themselves be covalently bonded either to the particle surface or to available functional groups on the hydrophobic or headgroup portion of the amphiphilic phospholipid molecules in the artificial membrane structure. A preferred group of membrane constituents which can be "loaded" into the immobilized membranes in accordance with this invention are phospholipids (i.e., a phospholipid phase having lateral mobility in the immobilized membrane), cholesterol, cholesterol esters and peptides, particularly those having a membrane-binding domain (i.e., a membrane binding amino acid sequence). The literature contains many references describing the sources and amino acid sequences of proteins known to adsorb to membrane interfaces, or to extend into or to project through natural biological membranes. When used as complementary constituents in the immobilized membrane-bearing chromatography supports of this invention, the interaction of such molecules in their "natural" environment with other substances can be studied by high, medium or low pressure liquid chromatography.

FIGS. 4 and 5 illustrate in some greater detail the structure of the preferred covalently bound artificial membranes in accordance with this invention. In the chemical formulas shown in FIGS. 4 and 5, Z represents a group of the formula $-OPO_2OR$ wherein R is selected from the group consisting of hydrogen, 2-aminoethyl, 2-(N-methyl)aminoethyl, 2-(N,N-dimethylamino)ethyl, 2-(trimethylammonium)ethyl, inosityl, glyceryl, 2-carboxy-2-aminoethyl and galactopyranosyl. The phospholipid molecules represented thereby are covalently bonded to the surface of particle 19 through covalent linkage 22. So bound, the phospholipid molecules collectively constitute an immobilized membrane having an inner hydrophobic region defined by hydrophobic portions 24 and 25 and an outer hydrophilic portion collectively defined by headgroups 14. When selecting phospholipid intermediates for covalent coupling with surfaces of particle supports, it is preferred that the hydrophobic portion 24 of the molecule, bearing a functional group intended for reaction with a functional group on the particle surface to form covalent linkage 22, be dimensioned so that the other hydrophobic portion 25 of that molecule has a length less than that of the functional group-bearing hydrophobic portion 24 so as not to present steric interference to covalent bond formation. In other words, the bonding hydrophobic portion 24 should provide enough distance between the support surface and the headgroup portion to allow the non-bearing hydrophobic portion 25 to extend toward the surface of particle 19 in its natural sterically unaffected conformation. Where the hydrophobic portion 25 is significantly longer than the functional group-bearing portion 24, such can interfere with preparation and possibly the functionality of the resulting covalently immobilized membrane structure.

FIG. 5 illustrates a covalently bound immobilized structure in accordance with this invention consisting of covalently bound lysophospholipid groups. In both of the structures depicted by FIGS. 4 and 5, except for the limitation mentioned above, the length of the hydrophobic portion 24, which can optionally have up to 3 points of unsaturation or branching, is not critical.

In the description of this invention there is used the chemical formula designation "OPO$_2$OR". That designation is intended to include both the protonated and unprotonated forms of the depicted phosphoric acid esters.

The covalently bound membrane structure illustrated in FIGS. 2, 4 and 5 can be conveniently synthesized from novel phospholipid carboxylic acids derived by the reaction of glycero-phosphatides or lysophospholipids and cyclic dicarboxylic anhydrides. Such novel artificial membrane-forming phospholipids can be illustrated by a group of the formula R$_6$CO(CH$_2$)$_n$COQ            I wherein n is an integer from 2 to 14
R$_6$ is -OH or 1-imidazolyl; and
Q is a group of the formula

or

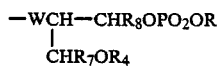

wherein R is selected from the group consisting of hydrogen, 2-aminoethyl, 2-(N-methyl)aminoethyl, 2-(N,N-dimethylamino)ethyl, 2-(trimethylammonium)ethyl, inosityl, glyceryl, 2-carboxy-2-aminoethyl and galactopyranosyl;

W is —O— or —NH—;

R$_4$ is hydrogen or an acyl group derived from a C$_2$–C$_{20}$ carboxylic acid, and R$_7$ is hydrogen and R$_8$ is hydrogen or R$_7$ and R$_8$ taken together with the carbon atoms to which they are bonded form a cyclopentane ring. Those compounds are prepared by the reaction of the corresponding lysophospholipids (derived, for example, by enzymatic hydrolysis of phospholipids with phospholipase A$_1$ or A$_2$), glycero-phosphatides, or the art-recognized 2-deoxy-2-amino analogues thereof (Chandrakumar and Hajdu, *J. Org. Chem.*, 1982, 47. 2144–2147) with a C$_4$–C$_{16}$ alkane dicarboxylic acid anhydride. The resulting carboxylic acid compound can be converted to an acylating form of that compound wherein R$_6$ is 1-imidazolyl by reaction with an equivalent amount of 1,1-carbonyldiimidazole. The functional group to form covalent bonds with a nucleophilic functional group, for example an amino group, on the surface of a chromatography support material. A preferred group of compounds in accordance with the above Formula I are those compounds formed by the reaction of a novel cyclic anhydride of the formula

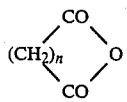    II wherein n is an integer from 8 to 14, with a lysophospholipid having an acyl group derived from a C$_{10}$–C$_{16}$ fatty acid.

The term C$_2$–C$_{20}$ carboxylic acid as used to describe this invention includes mono- and dicarboxylic acids, optionally having up to 3 points of unsaturation, preferably linear in molecular form but optionally having a cyclic or branched structure.

Surprisingly it was found that the 15-ring member cyclic anhydride represented by the above Formula II wherein n=12 could be prepared in high yields by reacting the corresponding dicarboxylic acid dissolved in warm (~40° C.) tetrahydrofuran with an equivalent amount of dicyclohexylcarbodiimide.

Chromatography support material can be prepared having covalently bound groups comprising phosphate diester groups group of the formula -CH$_2$OPO$_2$OR$_1$ wherein R$_1$ is selected from the group consisting of 2-aminoethyl, 2-(N-methylamino)ethyl, 2-(N,N-dimethylamino)ethyl, 2-(trimethylammonium)ethyl, 2-carboxy-2-aminoethyl, inosityl, glyceryl, and galactopyranosyl Chromatography supports bearing such phospholipid headgroup moieties provide a hydrophilic surface particularly useful for chromatography of substances showing selective affinity for the headgroup portions of phospholipid constituents of biological membranes. The nature of covalent linkage of the phosphate diester moiety to the surface of the chromatography support material is not critical; however, it can, depending on length of the linkage and chemical structure have a pronounced effect on the surface characteristics of the immobilized phosphate diester stationary phase. In a preferred embodiment the support material has a covalently bound glyceryl phosphate diester of the formula -OCH$_2$CHOR$_4$CH$_2$OPO$_2$R$_1$ wherein R$_4$ is hydrogen or an acyl group derived from a carboxylic acid. Again the length and nature of the covalent linkage between that group and the surface of the chromatography support material is not critical but can impact the chromatographic characteristics of the support material having such covalently bound groups.

In a more preferred embodiment the support material has covalently bound groups of the formula

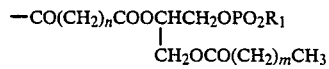

or

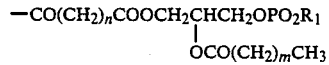

wherein n is an integer from 2 to 14 and m is an integer ≦ n. In still another preferred embodiment the support material has covalently bound groups of the formula

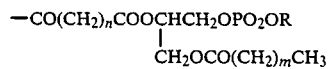

wherein n is an integer from 8 to 14. Such chromatography support materials can be prepared from phospholipid derived intermediates by reaction with cyclic anhydrides followed by conversion of the resulting carboxylic acid to an activated acylating agent using, for example, 1-1-carbonyldiimidazole and reacting the imidazolide intermediate with a commercially available support material having alcohol or amine groups for reaction and covalent bonding through an ester-forming or amide-forming nucleophilic displacement/condensation reaction.

The cyclic anhydrides of Formula II wherein n is an integer from 8 to 14 are valuable intermediates for the preparation of chromatography support materials having on its surface covalently bound functional groups. The cyclic anhydrides can be reacted with covalently bound nucleophilic groups on the surface of a commercially available chromatographic support material, for example, the propylamine groups of Nucleosil-300(7NH$_2$), subject only to steric limitations to provide a C$_8$ to C$_{14}$ substantially hydrophobic linking group terminating in a reactive carboxylic acid functional group. While chromatography support materials so modified have probable utility themselves as effective chromatography support materials for high pressure liquid chromatography, they also have a value as an intermediate wherein the terminal carboxy group can be used as a functional group for covalent bonding of other molecules having desirable properties for interaction with biomolecules in a chromatographic system. Thus the anhydride can serve as a convenient source of a divalent linking group of the formula —CO(CH$_2$)$_n$CO— wherein n is an integer from 8 to 14.

One example of the use of a cyclic anhydride of the Formula II as a source of a divalent linker is in the production of immobilized membranes in accordance with this invention. More particularly, the linker can be used to distance the membrane forming molecules from the support surface to provide a more "bi-layer like" immobilized membrane structure. Hereinabove the covalently bound immobilized membrane structures were described as comparable to one-half of a biological membrane bi-layer bound to the support surface. With use of a cyclic anhydride as a divalent linking group between the support surface and the membrane forming amphiphilic molecules, the immobilized membrane structure can be constructed to resemble more closely, at least in depth of the hydrophobic portion, a full membrane bi-layer. In sum, such a composition is prepared using the following steps: (1) react Nucleosil-300(7NH$_2$) with, for example, a cyclic dicarboxylic anhydride of the Formula II wherein n is 14 to provide a support material having a surface of covalently bound carboxy groups some 16–18 carbon atoms (including carbon atoms in the propylamine group) from the surface of the support structure; (2) react the product supports with 1,1-carbonyldiimidazole to form the corresponding imidazolide; (3) reacting the imidazolide-bearing support material with an excess (to minimize cross-linking) of ethylenediamine so that the linker on the surface of the Nucleosil-300(7NH$_2$) is represented by a group of the formula -CH$_2$CH$_2$CH$_2$NHCO(C$_2$)$_{1-2}$CONHCH$_2$CH$_2$NH$_2$; and (4) reacting the Product with, for example, the lecithin imidazolide prepared in the example below.

Bi-layer like immobilized artificial membranes can also be prepared by coupling to a particle surface art-recognized "boloamphiphiles" which are best described as two-headed amphiphiles, i.e., compounds having hydrophilic headgroups at each end of a long hydrophobic chain.

The immobilized membrane chromatography support materials in accordance with this invention can be used in a wide variety of chromatographic systems for purification of organic compounds. The support materials of the present invention can be used in traditional liquid solid chromatography applications as well as thin layer chromatography and high pressure liquid chromatography. The chromatographic substrates of this invention thus find application in a method for evaluating the membrane association characteristics of chemical compounds and for utilizing the membrane-association characteristics of chemical compounds to separate said compounds from compounds having dissimilar membrane-association characteristics. The method can be conducted advantageously in a high pressure liquid phase chromatography system. It is contemplated that HPLC chromatographic systems utilizing a stationary phase comprising an immobilized membrane structure consisting essentially of bound amphiphilic phospholipids and an immobilized biologically active protein can be utilized to identify substances of probable biological activity by providing a means for comparing the immobilized membrane association characteristics of test compounds with those characteristics of compounds known to have biological activity associated with the peptide in the immobilized membrane stationary phase. The protein constituent can be immobilized by covalent bonding, by its natural membrane affinity (for example, the protein itself can have transmembrane sequences) or by conversion to a membrane binding analogue as described above.

It is believed that the immobilized membrane stationary phases of the present invention offers the potential of identifying new drug leads. Such application of the present immobilized membrane substrates is predicated on the hypothesis that molecules binding to membrane constituents may have pharmacological activity, for example, by (1) changing the interfacial barrier allowing other drugs to reach cellular target sites; and/or (2) binding to the interfacial peptide membrane associated proteins. Binding drugs to interfacial peptides may result in perturbation of the immobilized protein constituent.

The implication of immobilized membranes in an HPLC drug discovery method is possibly the most significant application of the claim compositions. Drug discovery would identify molecules in the mobile phase that decrease the retention time of interfacial peptides on HPLC immobilized membrane columns. Such mobile phase-displacing ligands are potential drug leads. An alternate method of drug discovery would entail using, for example, Nucleosil-lecithin columns with or without a drug target site (e.g., a biologically active protein or functional sequence thereof immobilized with the immobilized membrane). Molecules that have longer retention times on columns containing the drug target sites are drug leads. This concept of HPLC-drug discovery using either immobilized membranes or traditional affinity columns is unprecedented in the art.

Other uses contemplated for the claimed immobilized membrane compositions include uses as solid supports for chromatographic separation of phospholipids and chiral amino acids and as a substrate for chiral synthesis. Because of the enhanced ability to elute proteins on the present immobilized membrane compositions utilizing predominantly aqueous mobile phases (as opposed to high solvent concentrations in reverse-phase chromatography systems), it is contemplated that the present membrane-bearing support materials will allow the non-denaturing separation of a wide variety of protein substances. In addition, there is a possibility that the present compositions will provide a stationary phase useful for separation or removal of endotoxins from contaminated protein samples. Further, because of the selective affinity of the immobilized membranes with membrane binding peptides it is contemplated that chromatographic systems utilizing immobilized membranes as a stationary phase can be used in resolving cell or viral homogenates for the production of multivalent vaccine formulations. Surface (membrane associated) protein fractions are those normally exposed to the body's antigen forming machinery. Thus the antigenic regions of viral protein associated with regions having high membrane affinity can be separated from the homogenate and utilized for vaccine production.

Chromatographic systems utilizing the present immobilized membrane supports is a tool for the isolation and purification of peptides and proteins. They find particular application for purification of the protein/peptide products of recombinant DNA research. Thus a protein expressed in a host cell transformed with a DNA expression vector capable of expressing said protein can be isolated from a cell lysate by chromatography techniques utilizing the present immobilized membrane support materials. While relatively little data has been generated on the chromatographic performance of immobilized membrane support materials, it is contemplated that chromatography of many peptides and proteins can be accomplished under non-denaturing aqueous mobile phase conditions.

The selective interaction between the present immobilized membrane supports and membrane binding peptides can be utilized with particular advantage in a generic purification method for proteins produced using recombinant DNA technology. Recombinant DNA techniques permits the production of functional proteins with covalently bound excess amino acids (polypeptides) wherein the physico-chemical properties of the resulting "hybrid polypeptide" facilitate the isolation and purification of the hybrid protein. Such extra amino acid sequence has denoted as a "purification handle", or "identification peptide", which is preferably linked to the desired protein through a selectively cleavable peptide linkage. Following purification of the "hybrid protein", using purification means which relies on the physico-chemical properties imparted to the hybrid molecules by the purification handle or identification peptide, that sequence (the purification handle/identification peptide) is cleaved from the desired protein at the predetermined intervening cleavage site. Such a technique for purifying proteins produced by genetically engineered microorganisms is described in U.S. Pat. No. 4,569,794, issued Feb. 11, 1986, and in U.S. Pat. No. 4,703,004, the disclosures of which are hereby expressly incorporated herein by reference.

U.S. Pat. No. 4,569,794 describes a process for separating a biologically active peptide or protein in the form of a precursor from a mixture containing said precursor and impurities by contacting the precursor with a resin containing immobilized metal ions. The precursor comprises a biologically active polypeptide or protein covalently linked directly or indirectly to an immobilized metal ion chelating peptide. The hybrid protein precursor is selectively eluted from the immobilized metal ion resin and optionally subjected to cleavage conditions to release the biologically active peptide following precursor purification. The '794 patent details the methodology for producing precursor hybrid molecules by recombinant DNA methodology.

U.S Pat. No. 4,703,004 describes a similar procedure wherein the purification handle, or the "identification peptide" as referred to in that patent, consists of a highly antigenic N-terminal portion and a C-terminal linking portion that connects the identification peptide to the N-terminal portion of a functional protein. The linking portion of the identification peptide is cleavable at a specific amino acid residue adjacent the functional protein by use of a sequence specific proteolytic enzyme or chemical proteolytic agent. The hybrid polypeptide expressed by the host cells transformed by the cloning vector is removed therefrom and purified by affinity chromatography techniques by use of an immobilized ligand specific to the antigenic portion of the identification peptide. The protein is then cleaved from the isolated hybrid polypeptide with an appropriate proteolytic enzyme or chemical agent, thereby releasing the mature functional protein in a highly purified, highly active state. A similar procedure has been described by T. Moke et al. in *Biochemistry.* 1987, 26, 5239–5244.

Utilizing the general procedures described in the '794 and '004 patents, hybrid polypeptides/proteins composed of an identification peptide having predictable membrane affinity and a desired functional protein can be produced by genetically engineered microorganisms, purified utilizing the immobilized membrane chromatography supports in accordance with this invention and thereafter selectively cleaved to provide the functional protein in a highly purified state.

Suitable membrane binding peptides which can be substituted for the immobilized metal ion chelating peptide in the procedure described in U.S. Pat. No. 4,569,794 or for the antigenic identification peptide utilized for the preparation of the hybrid polypeptides described in U.S. Pat. No. 4,703,004, are peptide sequences comprising a known membrane-binding sequence of a naturally occurring protein, for example, so-called "transmembrane sequences". The literature contains many references describing membrane-binding peptide sequences of biological proteins. The use of such natural peptide sequences, preferably sequences comprising about 10 to about 30 amino acids, cloned in tandem with a biologically functional protein, with an intervening cleavable peptide linkage is preferred. The use of membrane-binding peptides as a purification handle takes advantage of the natural affinity of such sequences for membrane environments to purify functional proteins which may not have, without the covalently bound membrane-binding purification handle, the requisite selective surface interaction with membrane surfaces to allow purification on the present immobilized artificial membrane supports. It is clear that the presently disclosed generic purification method has greater applicability for separation of proteins which themselves do not have high affinity for cell membrane surfaces.

It should be noted that membrane affinity of peptide sequences can be determined empirically as mentioned above, or they can be predicted by energy calculations or hydropathy plots as described by Hopp and Wood (1981), *Proceedings of the Natural Academy of Science.* 78:3824; or Kite and Doolittle (1982), *Journal of Molecular Biology.* 157:105. Thus, membrane affinity can be predicted from first principals. One example of a synthetic membrane binding peptide that can be used as a purification handle in accordance with the presently disclosed generic protein purification process is a 30-amino acid amphipathic peptide described by Subbarao et al. in *Biophysical Journal*, 49, 134a (1986) and designated by the authors as "P 100". P 100 has the following sequence: H-Trp-Glu-Ala-Ala-Leu-Ala-Glu-Ala-Leu-Ala-Glu-Ala-Leu-Ala-Glu-His-Leu-Ala-Glu-Ala-Leu-Ala-Glu-Ala-Leu-Glu-Ala-Leu-Ala-Ala-OH. It undergoes a random coil to alpha-helical conformation change as the pH is lowered from 7.6 to 4.2. The pH conformational sensitivity of that amphipathic peptide makes it uniquely adapted to use as a purification handle in accordance with this method. Thus, that peptide or a membrane-binding fragment thereof can be cloned in tandem to a biologically functional protein through a selectively cleavable peptide linkage such as those detailed in the above referenced patents. The resulting hybrid peptide has the general structure P 100 - cleavable peptide linker - functional peptide - OH.

The hybrid peptide can be purified by chromatography, for example in an HPLC system, utilizing the present immobilized membrane chromatography supports. Interaction of the peptide with the membrane-bearing support is controlled by adjustment of the pH of the mobile phase.

The properly designed hybrid protein produced by recombinant DNA methodology will contain a cleavage site at the junction of the desired product and the membrane binding portion. The cleavage site permits generation of mature product by chemical or enzymatic treatment of the hybrid protein product. Highly useful selective cleavge sites comprise a sequence of amino acids which can be cleaved chemically or enzymatically at its C-terminus.

Examples of chemical agents useful for cleaving proteins are cyanogen bromide, 2-(2-nitrophenylsulfenyl)-3-bromo-3'-methylindolinium (BPNPS-skatole), hydroxylamine, and the like. Cyanogen bromide cleaves proteins at the C-terminus of a methionine residue. Therefore, the selective cleavage site is a methionine residue itself. Hydroxylamine cleaves at the C-terminal of the moiety -Asn-B- in which B is Gly, Leu, or Ala. BNPS-skatole cleaves at the C-terminus of a tryptophan residue.

Examples of enzymatic agents useful for cleavage are trypsin, papain, pepsin, plasmin, thrombin, enterokinase, and the like. Each effects cleavage at a particular amino acid sequence which it recognizes. Enterokinase, for example, recognizes the amino acid sequence -(Asp)$_n$-Lys- in which n is an integer from 2 to 4.

The most preferred selective cleavage site, especially if the desired biologically active protein lacks methionine, is a methionine residue. This residue, joined to the N-terminus of the desired product, is readily cleaved by known methods using cyanogen bromide to produce the desired product.

Functional proteins which can be expressed as hybrid peptides having a membrane binding peptide sequence linked through a cleavable peptide linkage to the N-terminus of the functional peptide include growth hormone, insulin-like growth factor, glucagon, somatostatin, growth hormone releasing factor, interferon, interleukin 1, interleukin 2, tissue plasminogen activator and the like.

Preparation cf Immobilized Membrane Materials

Monomyristolyl lysolecithin was custom synthesized by Avanti Polar Lipids, Inc., Birmingham, Ala. The lysolecithin was prepared by diacylating glycero-phosphocholine followed by enzymatic cleavage of the C-2 position of the lecithin. Myristic acid 95% was used for the diacylation. The impurities, <2% in the final product, are $C_{16}$ and $C_{12}$ saturated fatty acids that have little influence on the final solid support.

1,3-Dicyclohexylcarbodiimide (DCC), 1,12-dodecanedicarboxylic acid, deuterium oxide, carbonyldiimidazole (CDI) were purchased from Aldrich Chemical Company. Infrared spectral grade potassium bromide (KBr) was also obtained from Aldrich. Nucleosil-300(7NH$_2$) was obtained from Rainin Inst. Co., Inc, Woburn, Mass. Nucleosil-300(7NH$_2$) is silica derivatized with propylamine groups at a surface density similar to that of the groups on support materials used for reverse phase chromatography columns.

All solvents were analytical grade. Dry tetrahydrofuran (THF) was prepared by distillation over calcium hydride. Dry chloroform (CHCl$_3$) was prepared from distillation over phosphorous pentoxide (Mallinckdrodt) and used within 24 hours of preparation. Dimethylaminopyridine (DMAP) obtained from Aldrich was crystallized from ethyl ether as follows: Eight g DMAP dissolved in 30 ml ethyl acetate was diluted with approximately 200 ml of ethyl ether. Refrigeration overnight precipitates DMAP which can be collected by filtration through a scintered glass funnel. The DMAP was dried overnight under vacuum at room temperature.

Lecithin is linked to the silica-based particle through an amide bond. The four step synthesis used to derivatize Nucleosil-300(7NH$_2$) with lecithin is summarized below.

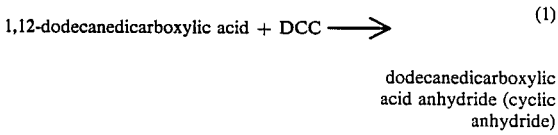

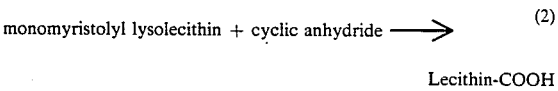

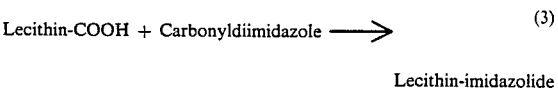

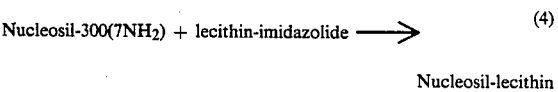

Procedure (1) 1,12-Dodecanedicarboxylic acid anhydride (cyclic anhydride).

A flame dried 500-ml round bottom flask was allowed to cool before 8 g (0.031 mole) of solid 1,12-dodecanedicarboxylic acid was added. Dry THF (~100 ml) was added to suspend the diacid. After stirring for 5-10 minutes the mixture was warmed with tap water to about 40° to effect dissolution of the diacid. A few particles were usually visible in the reaction flask at this point. DCC was weighed in a flame dried beaker. DCC (6.4 gm, 0.031 mole) was dissolved in 20 ml of THF. The concentrated DCC solution was transferred to the reaction vessel using a disposable pipette. Throughout all procedures the reaction vessel was purged with nitrogen. The reaction was sealed under nitrogen pressure and allowed to stir at room temperature for 15 hours. After 15 hours a thick, white paste formed and stopped the stirring bar. (Ideally, sufficient THF should be added initially to the reaction to prevent paste formation.) After 15 hours, 500 ml of reagent grade acetone was added followed by filtration through a scintered glass funnel (medium, 300 ml capacity). The filtrate was stored in the refrigerator overnight to crystallize the product. The cyclic anhydride was collected by filtration through a medium scintered glass funnel. The product was rinsed with reagent grade acetone and dried under vacuum, room temperature, overnight. Typical yields are 50–70% based only on the first crop of crystals. Reactions were monitored by FTIR using KBr pellets prepared from aliquots of the reaction mixture taken to dryness by rotoevaporation. See FIG. 6.

In preparations where formation of the cyclic anhydride was incomplete, small amounts (~200 mg) of DCC were added and the reaction allowed to continue. When the reaction was shown to be complete based on FTIR spectra, the reaction was stopped. It is difficult to separate the diacid from the anhydride, and therefore it is important to quantitatively form the cyclic anhydride.

Three different mass spectra obtained from three different reactions showed a parent ion $M+1=241$ indicative of formation of the cyclic anhydride and not the dimer. NMR of the product gave the expected peaks. (2) 1-Myristoyl-2-(13-carboxyl-tridecyloyl)-sn-3-glycero-phosphocholine (Lecithin-COOH).

Several pilot reactions were performed to optimize product formation Pilot studies showed the anhydride is virtually unreactive to lysolecithin without catalyst (DMAP). Four equivalents of anhydride appeared to give the best yields. Lysolecithin and the anhydride were dried overnight at the pump at 50° C. before use. Monomyristolyl lysolecithin, 3 g (6.4 mmole), 1,12-dodecanedicarboxylic acid anhydride, 6.5 g (27 mmole), and DMAP, 0.78 g (6.5 mmole) were added to a flamed dried 250-ml round bottom flask. Enough dry CHCl$_3$ (~200 ml) was added to completely dissolve the starting material. The solution was purged with nitrogen, sealed, and stirred in the dark for 48 hours. Thin layer chromatography (TLC) of the reaction mixture shows two spots for lecithin, and one minor spot for lysolecithin. The two lecithin spots correspond to the protonated and deprotonated form of lecithin-COOH. After work up of the reaction mixture only one spot for lecithin was observed by TLC. TLC analysis of lecithin analogs was performed in CHCl$_3$/MeOH/H$_2$O 65:25:2 using silica plates.

Figure 7:
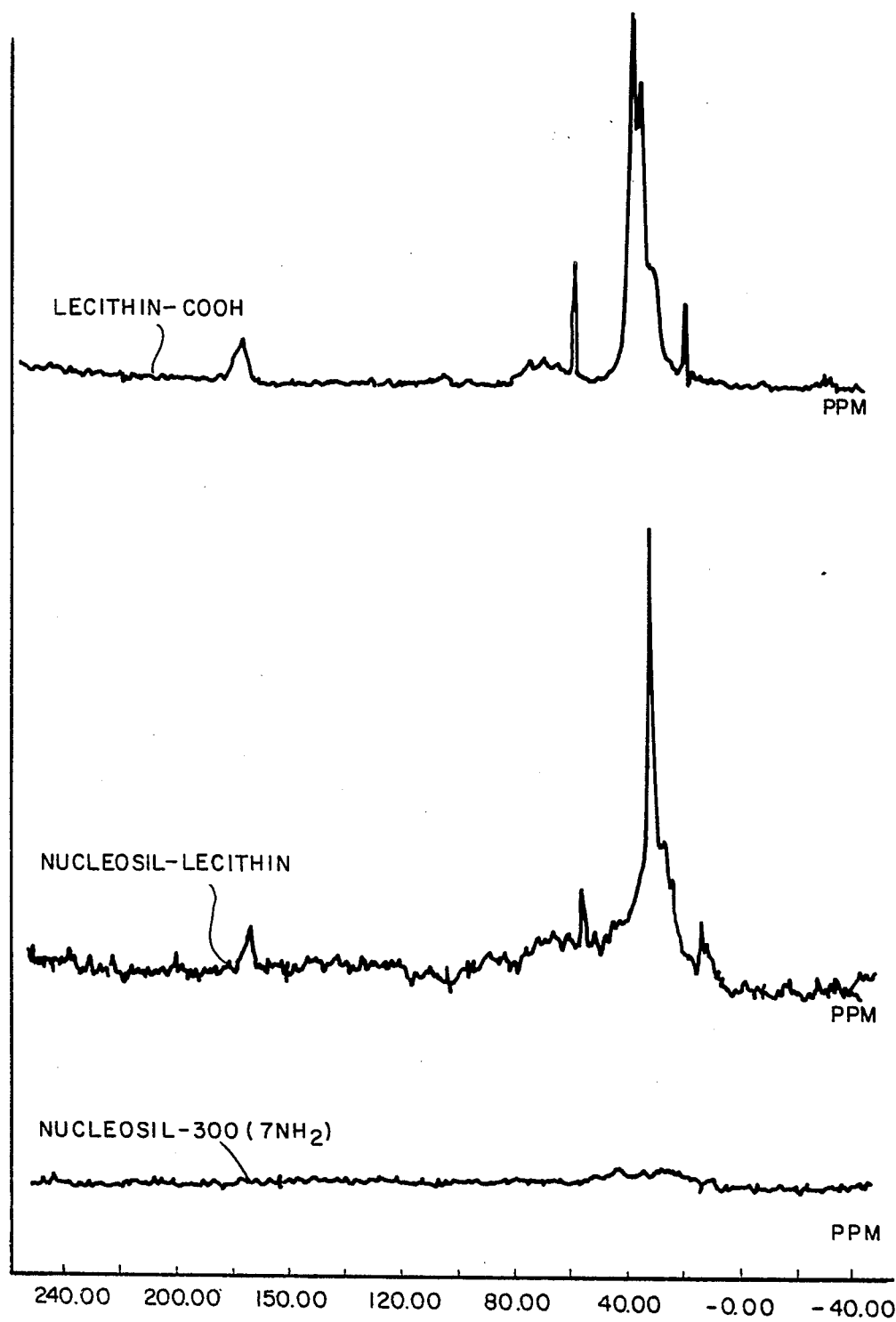
FIG. 7 shows $^{13}C$ solid state magnetic resonance spectra for a lecithin carboxylic acid and a chromatographic support of the invention.

After 48 hours the reaction has a slightly yellow tint. The reaction solvent (CHCl$_3$) was removed from the reaction mixture by rotoevaporation and ~20–30 ml of methanol was added to dissolve all solid. The methanol solution was filtered through a medium scintered glass filtration funnel. Approximately 800 ml of acetone was added to the methanolic solution of the product lecithin-COOH. Refrigeration of the acetone/methanol mixture precipitates lecithin and lysolecithin. During crystallization, product settles to the bottom of the flask. The supernatant was decanted and the lecithin was resuspended in approximately 50 ml of acetone before collecting the lecithin-COOH by filtration using a scintered glass funnel. Typical yields are ~65–80% lecithin-COOH contaminated with a trace of lysolecithin, and in one synthesis small amounts of DMAP. These contaminants do not interfere with the next coupling step and therefore were not removed. Final product purity was verified by TLC using the above solvent system. Lecithin purity was always >95% based on phosphate positive spots using Phospray (Supelco). Using TLC a comparison was made of the filtrate, the precipitate, DMAP and anhydride using MeOH:CHCl$_3$/1:9. Lecithin and lysolecithin remain at the origin. The anhydride exhibited RF=0.7; DMAP RF=0.15; and dodecanedicarboxylic acid, RF=0.4. In that system iodine was used to stain the TLC plates. C$^{13}$ NMR spectra were obtained on a Chemagnetics M200S solid state NMR spectrometer operating under the CPMAS mode at a frequency of 50,188 MHz. A decoupling field of 13 gauss was used and 2 K data points were collected over a spectral window of 300 ppm. Samples were spun at 3300 Hz. The contact time and the pulse delay were 2 milliseconds and 3 seconds respectively. Chemical shifts are relative to hexamethylbenzene as an external reference. The top spectrum in FIG. 7 is that for Lecithin-COOH.

(3) 1-Myristoyl-2-(13-carbonylimidazolide-tridecyloyl-sn-3-glycero-phosphocholin) (Lecithin-imidazolide).

The imidazolide of lecithin-COOH was prepared using carbonyldiimidazole. Side products in this reaction do not interfere with the next step and consequently lecithin-imidazolide was not purified before coupling lecithin to Nucleosil-300(7NH$_2$) in the final step. After flame drying and cooling, a scintillation vial or 50 ml round bottom flask was used for the coupling. Typically, lecithin-COOH (250 mg., 35 mmole) and carbonyldiimidazole (56.7 mg, 0.35 mmole) were reacted in dry CHCl$_3$ for 2 hours. The reaction was facile. TLC shows almost quantitative conversion of lecithin-COOH to the product lecithin-imidazolide. The lecithin-imidazolide was always used for coupling to the support material within 2 hours of preparation.

(4) Nucleosil-Lecithin.

Lecithin-imidazolide was coupled to Nucleosil-300(7NH$_2$) by two techniques; column perfusion of Nucleosil-300(7NH$_2$) with a solution of the lecithin-imidazolide, or stirring Nucleosil-300(7NH$_2$) with lecithin-imidazolide in a reaction flask. Both reactions were run overnight (~18 hours of total reaction time). For a few reactions the Nucleosil-300(7NH$_2$) particles were degassed prior to coupling. Degassing involved rotoevaporation of Nucleosil-300(7NH$_2$) suspended in 10 ml of dry CHCl$_3$. The degassing step was repeated at least twice but usually 3 times. Degassing was performed in the reaction container used to couple lecithin-imidazolide to Nucleosil-300(7NH$_2$). Typically, 1 gm Nucleosil-300(7NH$_2$) was stirred with 100 mg of lecithin imidazolide in dry CHCl$_3$ overnight.

Column Perfusion Method. A Bendex single piston pump (Model A-30-S) purchased from Rainin Inst. Co. was used for the column perfusion coupling technique. The single piston pump can perfuse from 0.05 to 1.5 ml/min at pressures up to 5000 psi. These operating conditions are similar to analytical HPLC conditions. An outdated HPLC column was emptied of its original packing material and Nucleosil-300-7NH$_2$ (1g) was added as a CHCl$_3$ slurry using a disposable pipette. The old analytical column was cleaned and dried before use, and the original frit (5 micron cutoff) was used to retain the Nucleosil-300(7NH$_2$) Packing material to be derivatized. Dry CHCl$_3$ was circulated through the column before a lecithin-imidazolide solution was substituted for the solvent in the reservoir. Lecithin-imidazolide (250 mg) in CHCl$_3$ (~5 ml) was substituted for the solvent reservoir to initiate coupling of lecithin-imidazolide to Nucleosil-300(7NH$_2$). Perfusion conditions were ~1.5 ml/min overnight.

Each of the described coupling methods resulted in an efficient coupling to Nucleosil-300 7NH$_2$. Each method resulted in a surface density of covalently bonded lecithin near that in biological membranes. Double coupling to the Nucleosil-300 (i.e., attempting a second coupling reaction using the previously coupled product) result in a modest increase in umol of lecithin bonded. See Table 1. Approximately 10-15% lecithin is coupled in the second coupling reaction. The second coupling step can permit formation of a membrane-like surface containing two different lipids, if a different lipid is used in the second coupling. For instance, phosphatidylethanolamine, phosphatidylserine, or phosphatidic acid may be coupled in the second step to generate charged surfaces. Thus phosphatidylcholine and phosphatidylethanolamine at an approximate ratio of 9/1 may be covalently linked to Nucleosil-300(7NH$_2$) if the first coupling reaction utilizes lecithin, and the second coupling reaction utilizes phosphatidylethanolamine. Of course, phosphatidylcholine and phosphatidylethanolamine will, like the bonded phosphatidylcholine, need to be derivatized to contain appropriate functional groups at or near the terminal end of at least one of their fatty acid chains to link the lipids to the solid support. Alternatively the second phospholipid composition can be loaded onto the once-reacted Nucleosil-300(7NH$_2$) product to form a heterogenous membrane structure having Partial lateral mobility.

The total surface area of silica is based on gas adsorption isotherms. However, only part of this surface is accessible to bonding organic molecule. The amount of surface area accessible for bonding depends on the size of the organic group to be bonded. all reactions, (—) the degas step was omitted from every reaction, (— +) the first reaction was not degassed but the second reaction was degassed.
$^{(a)}$The value in parenthesis reflects the mg-lecithin per gram of Nucleosil-lecithin.

Figure 8:
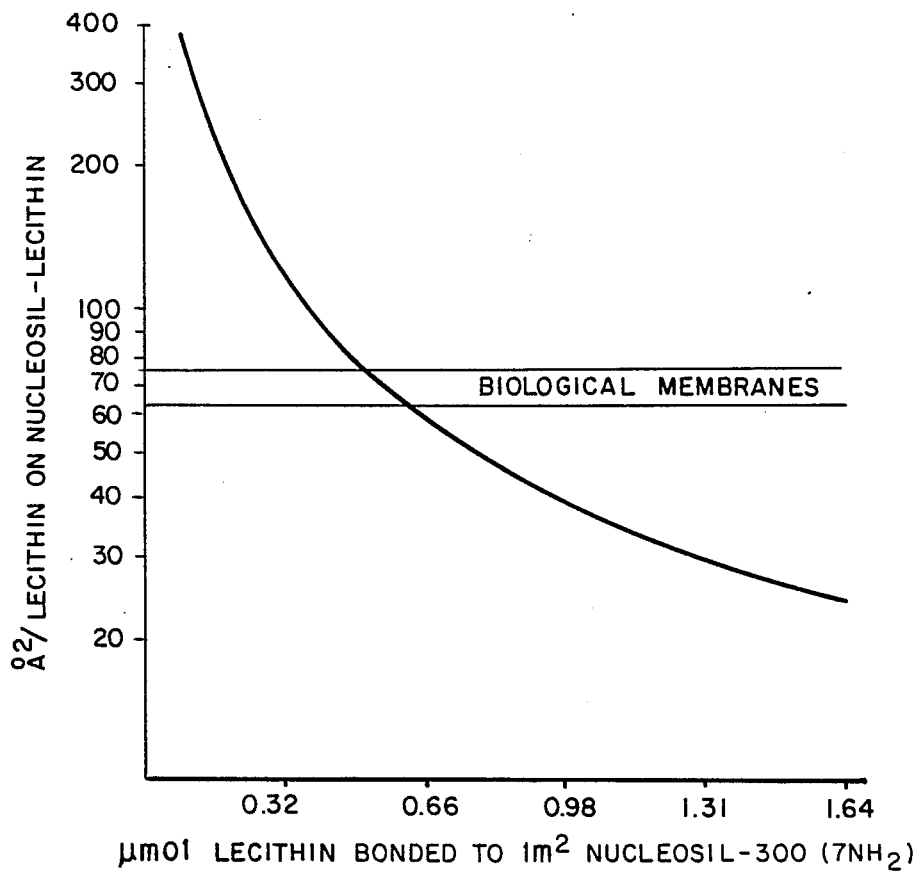
FIG. 8 is a graphic illustration of the relationship between micromoles of bonded lecithin to the surface of Nucleosil-300(7NH$_2$) and the area in square Angstroms per molecule of lecithin on the support surface.
Figure 9:
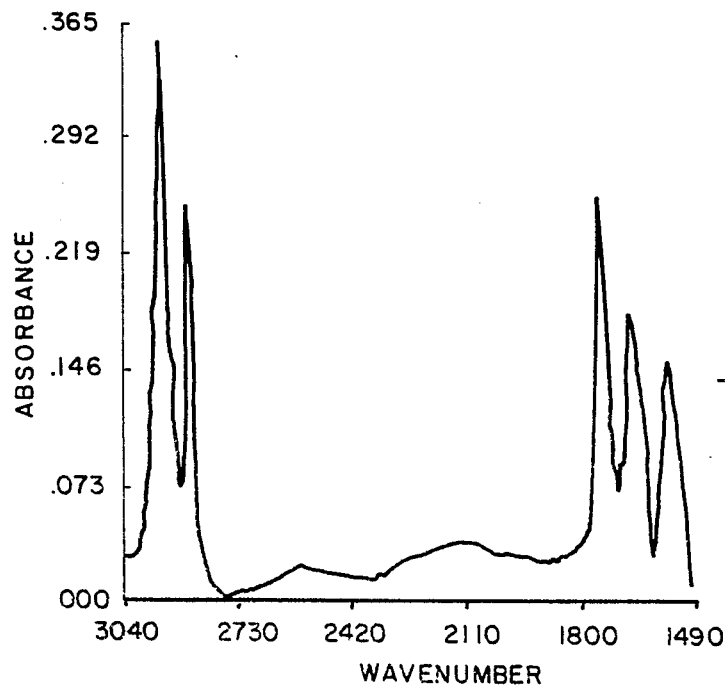
FIG. 9 is a reflectance IR spectrum of an immobilized membrane bearing support of the invention.

Usually, steric constraints limit the amount of organic molecules that can be bonded. For instance, small molecular weight gases may have access to minute crevices that larger organic molecules like propylamine, do not have access to. Nucleosil-300(7NH$_2$) has 100 m$^2$/g (manufacturers specification). Elemental analysis of Nucleosil-300(7NH$_2$) showed 1.64 umol-propylamine/m$^2$ to be bonded. For calculation of the area/molecule of lecithin, assume that 1.64 umol/m$^2$ propylamine density to be the available surface density at close packing. Looking down the long axis, straight chain alkanes have a projected surface area of 20-25 square Angstroms. Lecithin in biological membranes occupies 66-77 square Angstroms. Thus the limiting amount of lecithin that can be bonded is approximately ⅓ of the available propylamine groups. FIG. 8 shows the estimated area/molecule calculations based on these assumptions. A comparison of the results in Table 1 with the graphical presentation in FIG. 8 reveals that the Nucleosil-lecithin product has a surface density of covalently bound lecithin molecules comparable to that found in biological membranes. Preferably lecithin is covalently bound at a level sufficient to provide about 1 to about 2, more preferably about 1.3 to about 1.6 molecules per 100 square Angstroms of support surface area. The unreacted amine groups on the Nucleosil-300(7NH$_2$) surface can be capped with organic functional groups, if desired. Reflectance IR of the product Nucleosil-lecithin confirmed presence of linking amide bond: See FIG. 9 – amide I at 1653.9 cm$^{-1}$ and amide II at 1550.9 cm$^{-1}$ C$^{13}$NMR of the nucleosil-lecithin further confirmed the presence of the bonded lecithin stationary phase. See FIG. 7. Nucleosil-Lecithin tested phosphate-positive with "Phospray" (Supelco) Bellefonte, PA.

Column Packing

A 4 mm×100 mm HPLC column was packed with about one gram of Nucleosil-lecithin (pooled from several preparations above) using a Shandon column packer. Excess Nucleosil-lecithin (1.45 grams) was suspended in 15 ml of degassed methanol and then sonicated 5 minutes to assure particle dispersion. The dispersion was transferred to the 30-ml slurry reservoir on the column packer, and 15 ml of degassed methanol was added to fill the reservoir. The column was packed at 4500 psi.

The HPLC elution properties of the Nucleosil-lecithin column were evaluated.

A. Separation of d-Phenylalanine and l-Tryptophan.

Figure 10:
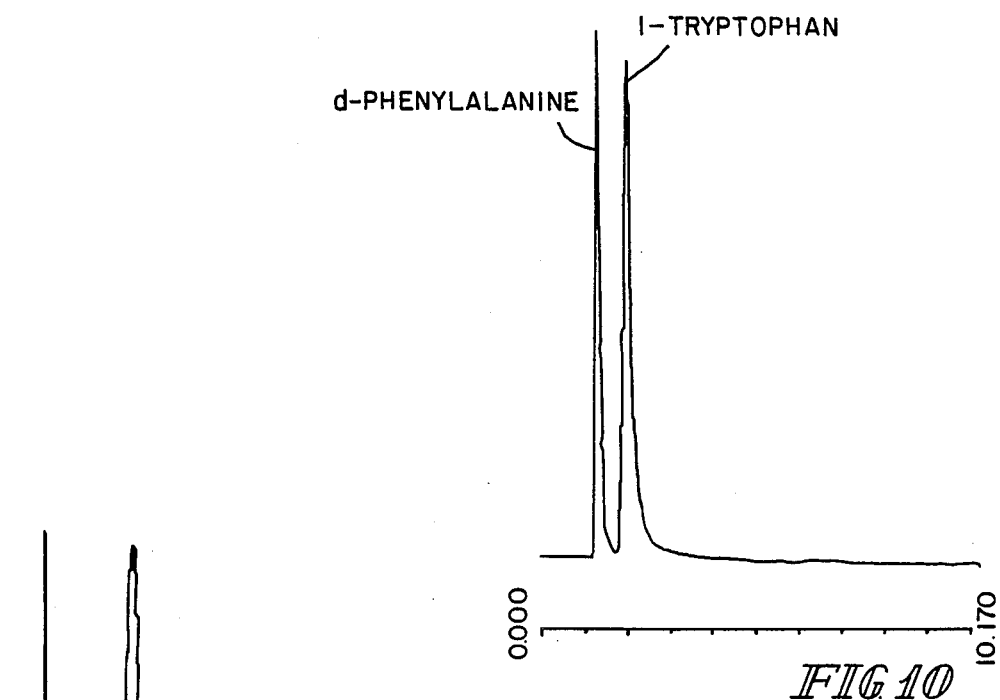
FIGS. 10, 11 and 12 are chromatograms showing separation of compounds on an HPLC column utilizing a support material of the invention.

FIG. 10 shows the separation of d-phenylalanine and l-tryptophan using isotonic phosphate buffered saline (1 ml/min) as the mobile phase with detection at 260 nm. The amino acids were identified from HPLC chromatograms of the pure amino acids. Enantiomeric mixtures of phenylalanine and tryptophan could not be resolved on this system.

B. Separation of Deoxynucleosides.

Separation of 2-deoxycytidine (C), 2-deoxyuridine (U), 2'-deoxyguanosine (G) and 2'-deoxyadenosine (A) was effected using isotonic buffered saline as the mobile phase at 1.0 ml/min with detection at 260 nm. Elution times were as follows: C - 1.175; U - 1.465; G - 1.730; and A - 2.090.

C. Several elution studies were made with the following peptides:

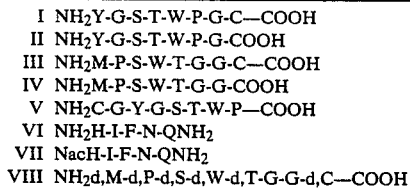

| | |
|---|---|
| I | NH$_2$Y-G-S-T-W-P-G-C—COOH |
| II | NH$_2$Y-G-S-T-W-P-G-COOH |
| III | NH$_2$M-P-S-W-T-G-G-C—COOH |
| IV | NH$_2$M-P-S-W-T-G-G-COOH |
| V | NH$_2$C-G-Y-G-S-T-W-P—COOH |
| VI | NH$_2$H-I-F-N-QNH$_2$ |
| VII | NacH-I-F-N-QNH$_2$ |
| VIII | NH$_2$d,M-d,P-d,S-d,W-d,T-G-G-d,C—COOH |

Peptide VIII is the d isomer of Peptide III. Peptide I and Peptide II differ by a cysteine on the C-terminus. Peptide III and Peptide IV differ by a cysteine on the C-terminus. Peptide I and Peptide V have the same amino acids in different order, and Peptide VII is Peptide VI with an N-acetyl group at the N-terminus.

Figure 11:
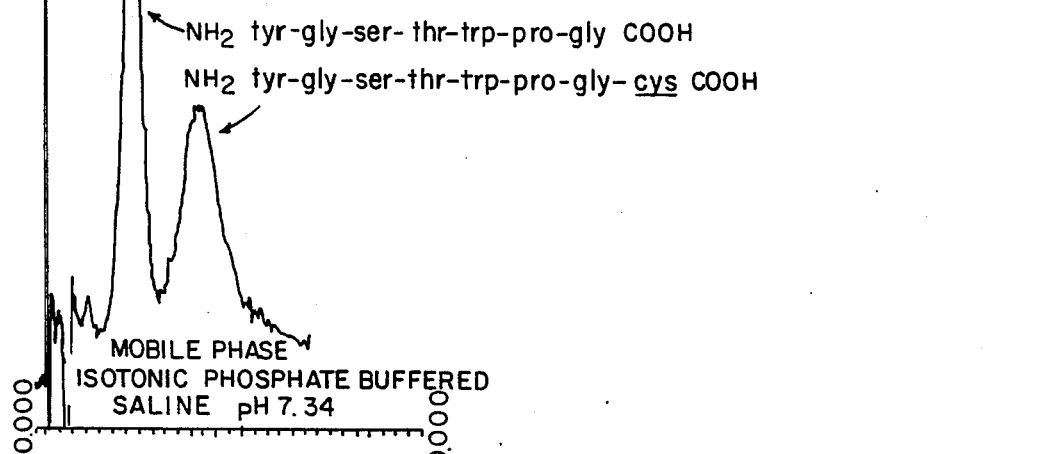
Figure 12:
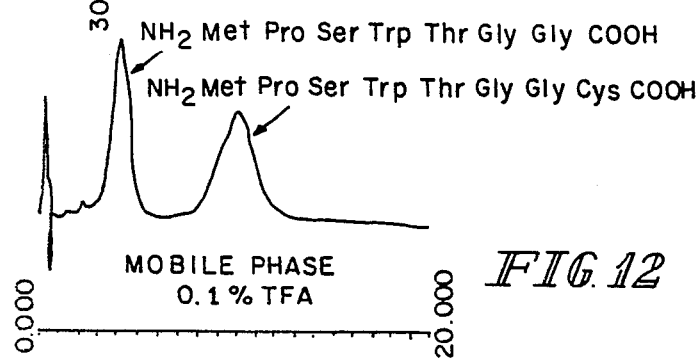

FIG. 11 is a chromatogram for a mixture of Peptides I and II, dissolved in 0.1% aqueous trifluoracetic acid (TFA) and detected at 220 nm. In FIG. 11 the mobile phase was isotonic phosphate buffered saline (pH 7.34). FIG. 12 is a chromatogram for a mixture of Peptides III and IV, dissolved in 0.1% aqueous trifluoracetic acid (TFA) and detected at 220 nm. In FIG. 12 the mobile phase was 0.1% TFA.

Elution volumes for Peptides I-IV, VI and VII are shown in Table 2 below.

TABLE 2

| | Elution Volumes on Nucleosil-Lecithin | |
|---|---|---|
| | Mobile Phase | |
| Peptide | 0.1% TFA | PBS |
| I | 7.3 | 13.1 |
| II | 3.1 | 7.6 |
| III | 9.4 | 10.0 |
| IV | 4.1 | 4.2 |
| VI | | 5.8 |
| VII | | 3.8 |

Cholesterol Loading.

The Nucleosil-lecithin chromatography support material was then "loaded" with cholesterol in situ using the following procedure.

A solution of 80 ml of 1 mg/ml cholesterol in MeOH-:isopropanol/8:2 was pumped through the Nucleosil-lecithin using a Bendex pump. The column effluant was reduced in volume to quantitate cholesterol that did not associate with the column. Approximately mg was recovered in the effluent showing that 40 mg of cholesterol was loaded onto the Nucleosil-lecithin column. This is approximately 50% by weight of the bonded phase. The Nucleosil-lecithin/cholesterol column containing MeOH/isopropanol was attached to the HPLC and eluted with water (approximately 100 ml). The mobile phase was changed to 0.1% TFA and peptides dissolved in 0.1% TFA were injected to determine the elution volumes. The mobile phase was changed to water and the peptides were reinjected after the column was equilibrated with 100 ml of water to determine the elution volumes. The column was washed with PBS buffer (100 ml) and the peptides were again injected to determine elution volumes using PBS as the mobile phase. The results are listed in Table 3.

TABLE 3

| Column: Nucleosil-Lecithin/Cholesterol | | | |
|---|---|---|---|
| | Elution Volumes by Mobile Phase | | |
| Peptide | $H_2O$ | 0.1% TFA | PBS |
| I | 7.3 | 5.3 | 7.9 |
| II | 6.6 | 2.7 | 4.8 |
| III | 9.2 | 5.3 | 6.9 |
| IV | 4.9 | 2.9 | 5.0 |
| V | | 6.6 | |
| VI | 0.8 | 1.0 | 4.2 |
| VII | 0.8 | 1.3 | 3.2 |
| VIII | 3.0 | 5.0 | 6.5 |

After approximately 50 injections using aqueous solvent as mobile phase the column was eluted with MeOH to remove cholesterol from the column. This column wash generated only approximately 3 mg of cholesterol. Approximately 4 liters of aqueous mobile phase had passed through the column during this study; the cholesterol apparently was gradually eluted from the column.

I claim:

1. A composition of matter comprising
a particulate support material,
a synthetic membrane structure on the surface of said support material, said membrane structure comprising a hydrophilic outer portion and a hydrophobic inner portion and further comprising a layer of molecules of an amphiphilic compound, said molecules having hydrophilic and hydrophobic portions forming the outer and inner portions, respectively, of the membrane structure, said amphiphilic compounds selected from the group consisting of amphiphilic compound constituents of biological cell membranes and liposome-forming amphiphilic compounds, and
means for immobilizing the membrane structure on the surface of the support material.

2. The composition of claim 58 wherein the means for immobilizing the membrane structure on the surface of the support material comprises divalent functional groups covalently bonded to the surface of the support material and to the amphiphilic molecules forming the membrane structure.

3. The composition of claim 1 wherein the particulate support material is selected from the group consisting of silica, alumina, titania, and resin based chromatographic support material having a particle size from about 5 to about 100 microns in diameter.

4. The composition of claim 3 wherein the particulate support material has a substantially hydrophobic surface and the means for immobilizing the membrane structure comprises hydrophobic interaction of the hydrophobic surface and the hydrophobic portion of the amphiphilic molecules in said membrane structure.

5. The composition of claim 4 wherein the substantially hydrophobic surface of the particulate support structure is the hydrophobic portion of a second amphiphilic compound covalently linked to the particulate support structure through a functional group on the hydrophilic portion of said compound.

6. The composition of claim 4 wherein the hydrophobic portion of the amphiphilic molecules bears a functional group capable of forming covalent bonds with a second functional group on the substantially hydrophobic surface of the particulate support.

7. The composition of claim 4 wherein the amphiphilic compound is selected from the group consisting of lecithins, lysolecithins, cephalins, sphingomyelin, cardiolipin, glycolipids, gangliosides and cerebrosides.

8. The composition of claim 4 wherein the amphiphilic compound is selected from the group consisting of phosphatidylcholine, phosphatidylethanolamine, N-methyl phosphatidylethanolamine, N,N-dimethylphosphatidylethanolamine, phosphatidic acid, phosphatidylserine, phosphatidylinositol and phosphatidylglycerol and the corresponding lysophospholipid derivatives.

9. The composition of claim 8 wherein the amphiphilic compound is a phospholipid and hydrophobic portion of the phospholipid molecules has at least one functional group for crosslinking the phospholipid molecules forming the synthetic membrane structure.

10. The composition of claim 9 wherein the amphiphilic compound is phosphatidylcholine, the hydrophobic portion of said compound comprising a diacetylenic $C_8$-$C_{26}$ hydrocarbon chain having conjugated di-yne groups crosslinkable upon actinic irradiation.

11. The composition of claim 1 wherein the particulate support has a surface comprising a first functional group and the hydrophobic portion of the amphiphilic compound bears a second functional group capable of reacting with and forming covalent bonds with said first functional group, said means for immobilizing the membrane structure comprising covalent bonds between the first and second functional groups.

12. The composition of claim 11 wherein said first and second functional groups are selected so that said covalent bonds are selected from the group consisting of ester, ether and amide bonds.

13. The composition of claim 11 wherein the amphiphilic compound is a phospholipid.

14. The composition of claim 11 wherein the amphiphilic compound is selected from the group consisting of lecithins, lysolecithins, cephalins, sphingomyelin, cardiolipin, glycolipids, gangliosides and cerebrosides.

15. The composition of claim 14 wherein the amphiphilic compound is selected from the group consisting of phosphatidylcholine, phosphatidylethanolamine, N-methylphosphatidylethanolamine, N,N-dimethylphosphatidylethanolamine, phosphatidic acid, phosphatidylserine, phosphatidylinositol and phosphatidylglycerol.

16. The composition of claim 11 wherein the amphiphilic compound is selected from the group consisting of phosphatidylcholine, phosphatidylethanolamine, N-methyl phosphatidylethanolamine, N,N-dimethylphosphatidylethanolamine, phosphatidic acid, phosphatidylserine, phosphatidylinositol and phosphatidylglycerol.

17. The composition of claim 16 wherein the amphiphilic compound is covalently bound to the surface in an amount sufficient to cover the surface of the support structure at a concentration about 1 to about 2 molecules of amphiphilic compound per 100 square Angstroms of surface area of the support structure.

18. The composition of claim 17 wherein the particulate support structure is a silica, alumina, titania or resin based chromatographic support material having a particle size from about 5 to about 100 microns.

19. The composition of claim 11 wherein the immobilized membrane structure further comprises an absorbed component selected from the group consisting of lipids, peptides, saccharides, oligonucleotides, polynucleotides and membrane-binding analogues of peptides, saccharides, oligonucleotides and polynucleotides.

20. The composition of claim 19 wherein said adsorbed component is selected from the group consisting of phospolipids, cholesterol, cholesterol esters and peptides having a membrane binding amino acid sequence.

21. The composition of claim 11 wherein the amphiphilic compound is a phospholipid covalently bound in an amount sufficient to cover the surface of the support structure at a concentration of about 1.0 to about 2.0 molecules of phospholipid per 100 square Angstroms of surface area of the support structure.

22. The composition of claim 11 wherein the amphiphilic compound is phosphatidylcholine covalently bound in an amount sufficient to cover the surface of the support structure at a concentration of about 1.3 to about 1.6 molecules per 100 square Angstroms of surface area of the support structure.

23. The composition of claim 22 wherein cholesterol is adsorbed in the immobilized membrane structure formed by the covalently bound phosphatidylcholine.

24. A method for utilizing the membrane-association characteristics of chemical compounds to separate said compounds from compounds having dissimilar membrane-association characteristics, said method comprising the steps of contacting said compounds with the surface of a synthetic membrane-bearing chromatography support material in the presence of a mobile phase and separating said mobile phase from said chromatography support material, said chromatography support material comprising
a support surface,
a synthetic membrane structure on the support surface, and
means for immobilizing the membrane structure on the support surface, said membrane structure comprising a hydrophilic outer portion and a hydrophobic inner portion and further comprising a layer of molecules of an amphiphilic compound, said molecules having hydrophilic and hydrophobic portions forming the outer an dinner portions, respectively, of the membrane structure, said amphiphilic compounds selected from the group consisting of amphiphilic compound constituents of biological cell membranes and liposome-forming amphiphilic compounds.

25. The method of claim 24 wherein the support surface is substantially hydrophobic and the means for immobilizing the membrane structure comprises hydrophobic interaction of the surface and the hydrophobic portion of the amphiphilic molecules forming said membrane structure.

26. The method of claim 25 wherein the amphiphilic compound is selected from the group consisting of phosphatidylcholine, phosphitidylethanolamine, N-methyl phosphatidylethanolamine, N,N-dimethylphosphatidylethanolamine, phosphatidic acid, phosphatidylserine, phosphatidylinositol and phosphatidylglycerol.

27. The method of claim 26 wherein the hydrophobic portion of said amphiphilic compound has at least one functional group for crosslinking the molecules of the amphiphilic compound forming the artificial membrane structure whereby said crosslinking functions to assist immobilization of said membrane structure on the support surface.

28. The method of claim 24 wherein the support surface comprises a first functional group and the hydrophobic portion of the amphiphilic compound has a second functional group capable of reacting with and forming covalent bonds with said first functional group, said means for immobilizing the membrane structure comprising covalent bonds between the first and second functional groups.

29. The method of claim 28 wherein said first and second functional groups are selected so that they react to form covalent bonds selected from the groups consisting of ether bonds, amide bonds, and ester bonds.

30. The method of claim 24 wherein the means for immobilizing the membrane structure on the support surface comprises divalent functional groups covalently bonded to the support surface and to the amphiphilic molecules forming the membrane structure.

31. The method of claim 30 wherein the amphiphilic compound is selected from the group consisting of lecithins, lysolecithins, cephalins, sphingomyelin, cardiolipin, glycolipids, gangliosides and cerebrosides.

32. The method of claim 31 wherein the amphiphilic compound is selected from the group consisting of phosphatidylcholine, phosphatidylethanolamine, N-methyl phosphatidylethanolamine, N,N-dimethylphosphatidylethanolamine, phosphatidic acid, phosphatidylserine, phosphatidylinositol and phosphatidylglycerol.

33. The method of claim 24 wherein the chemical compounds are derived from a cell or a viral homogenate and wherein a membrane binding-fraction of said homogenate is separated for use in a multivalent vaccine formulation.

34. The method of claim 24 wherein the chemical compounds are proteins.

35. The method of claim 24 wherein the protein is one expressed in a host cell transformed with a DNA expression vector capable of expressing said protein.

36. The method of claim 35 wherein the protein is a hybrid polypeptide comprising a membrane-binding amino acid sequence coupled to a biologically active protein.

37. The method of claim 36 wherein the hybrid polypeptide further comprises a protease cleavable or chemically cleavable linking portion between the membrane-binding sequence and the protein.

38. A method for evaluating the membrane-association characteristics of a chemical compound, said method comprising the steps of contacting said compound with the surface of a synthetic membrane-bearing chromatography support material in the presence of a mobile phase, and separating said mobile phase from said chromatography support material, said synthetic membrane-bearing chromatography support material comprising
a support surface,
a synthetic membrane structure on the support surface, and means for immobilizing the membrane structure on the support surface, said membrane structure comprising a hydrophilic outer portion and a hydrophobic inner portion and further comprising a layer of molecules of an amphiphilic compound, said molecules having hydrophilic and hydrophobic portions forming the outer and inner portions, respectively, of the membrane structure, said amphiphilic compounds selected from the group consisting of amphiphilic compound constituents of biological cell membranes and liposome-forming amphiphilic compounds.

39. The method of claim 38 wherein the means for immobilizing the membrane structure on the support surface comprises divalent functional groups covalently bonded to the support surface and to the amphiphilic molecules forming the membrane structure.

40. The method of claim 38 wherein the support surface is substantially hydrophobic and the means for immobilizing the membrane structure comprises hydrophobic interaction of the surface and the hydrophobic portion of the amphiphilic molecules forming said membrane structure.

41. The method of claim 40 wherein the amphiphilic compound is selected from the group consisting of phosphatidylcholine, phosphitidylethanolamine, N-methyl phosphatidylethanolamine, N,N-dimethylphosphatidylethanolamine, phosphatidic acid, phosphatidylserine, phosphatidylinositol and phosphatidylglycerol.

42. The method of claim 41 wherein the hydrophobic portion of said amphiphilic compound has at least one functional group for crosslinking the molecules of the amphiphilic compound forming the artificial membrane structure whereby said crosslinking functions to assist immobilization of said membrane structure on the support surface.

43. The method of claim 38 wherein the support surface comprises a first functional group and the hydrophobic portion of the amphiphilic compound has a second functional group capable of reacting with and forming covalent bonds with said first functional group, said means for immobilizing the membrane structure comprising covalent bonds between the first and second functional groups.

44. The method of claim 43 wherein said first and second functional groups are selected so that they react to form covalent bonds selected from the group consisting of ether bonds, amide bonds, and ester bonds.

45. The method of claim 39 wherein the amphiphilic compound is selected from the group consisting of lecithins, lysolecithins, cephalins, sphingomyelin, cardiolipin, glycolipids, gangliosides and cerebrosides.

46. The method of claim 46 wherein the amphiphilic compound is selected from the group consisting of phosphatidylcholine, phosphatidylethanolamine, N-methyl phosphatidylethanolamine, N,N-dimethylphosphatidylethanolamine, phosphatidic acid, phosphatidylserine, phosphatidylinositol and phosphatidylglycerol.

47. The method of claim 46 wherein the immobilized membrane structure further comprises a component selected from the group consisting of lipids, peptides, saccharides, oligonucleotides, polynucleotides and membrane-binding analogues of peptides, saccharides, oligonucleotides and polynucleotides.

48. The method of claim 47 comprising the additional step of comparing the membrane association characteristics of said chemical compounds with those characteristics of known biologically active compounds to identify chemical compounds of probable biological activity.

49. The method of claim 38 wherein the immobilized membrane structure further comprises a component selected from the group consisting of lipids, peptides, saccharides, oligonucleotides, polynucleotides and membrane-binding analogues of peptides, saccharides, oligonucleotides and polynucleotides.

50. The method of claim 47 wherein the component comprises a polypeptides segment of a transmembrane domain of a biologically active protein.

51. The method of claim 47 comprising the additional step of comparing the membrane association characteristics of said chemical compounds with those characteristics of known biologically active compounds to identify chemical compounds of probable biological activity.

52. A chromatography support material comprising a particulate support and a membrane mimetic structure comprising phosphate diester groups of the formula $-CH_2OPO_2OR_1$ covalently bonded to the surface of said support material, wherein $R_1$ is selected from the group consisting of 2-aminoethyl, 2-(N-methylamino)ethyl, 2-(N,N-dimethylamino)ethyl, 2-(trimethylammonium)ethyl, 2-carboxy-2-aminoethyl, inosityl, glyceryl, and galactopyranosyl.

53. The support material of claim 52 having covalently bound groups of the formula

or

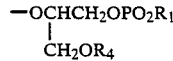

wherein $R_4$ is hydrogen or acyl group derived from a carboxylic acid.

54. The support material of claim 53 having covalently bound groups of the formula

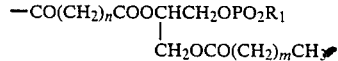

or

-continued

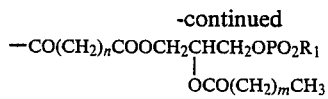

wherein n is an integer from 2 to 14 and m is an integer $\leq n$.

55. The support material of claim 54 wherein the covalently bound groups are of the formula

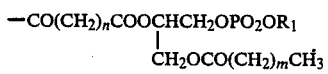

wherein n is an integer from 8 to 14.

56. In a chromatographic system comprising a mobile phase and a solid chromatography support material having a stationary phase on the surface of said support material, the improvement consisting essentially of forming said stationary phase as a synthetic membrane immobilized on the surface of the support material, said synthetic membrane comprising a hydrophilic outer portion and a hydrophobic inner portion and further comprising a layer of molecules of an amphiphilic compound, said molecules having hydrophilic and hydrophobic portions forming the outer and inner portions, respectively, of the synthetic membrane stationary phase, said amphiphilic compounds selected from the group consisting of amphiphilic compound constituents of biological cell membranes and liposome-forming amphiphilic compounds.

57. The improvement of claim 56 wherein the amphiphilic molecules forming the synthetic membrane stationary phase are covalently bonded to the surface of the support material.

* * * * *

UNITED STATES PATENT AND TRADEMARK OFFICE
CERTIFICATE OF CORRECTION

PATENT NO. : 4,931,498

DATED : June 5, 1990

INVENTOR(S) : Pidgeon

It is certified that error appears in the above-identified patent and that said Letters Patent is hereby corrected as shown below:

In column 2, line 8, replace "chromatogrpahic" with --chromatographic--.

In column 4, line 46, after "amphiphilic", insert --molecules--.

In column 5, line 20, replace "hydrOphobiC" with --hydrophobic--.

In column 9, line 55, after "The", insert --resulting imidazolide can be used as a reactive--.

In column 10, line 22, after "topyranosyl", insert --.--.

In column 11, line 56, replace "Product" with --product--.

In column 15, line 64, replace "cf" with --of--.

In column 17, line 32, after "formation", insert --.--.

In column 18, line 63, replace "Packing" with --packing--.

In column 19, line 30, replace "Partial" with --partial--.

UNITED STATES PATENT AND TRADEMARK OFFICE
CERTIFICATE OF CORRECTION

PATENT NO. : 4,931,498

DATED : June 5, 1990

INVENTOR(S) : Pidgeon

It is certified that error appears in the above-identified patent and that said Letters Patent is hereby corrected as shown below:

In column 19, between lines 30 and 31, insert

— TABLE 1

SPECIFIC SURFACE COVERAGE OF LECITHIN
ON NUCLEOSIL-LECITHIN[a]

| Degas particles[d] | Non-perfusion coupling[b] $\mu$mol-lecithin/$m^2$-Nucleosil | | Perfusion coupling[c] $\mu$mol-lecithin/$m^2$-Nucleosil | |
|---|---|---|---|---|
| | First coupling | Second coupling | First coupling | Second coupling |
| + | 0.620(46.2)[e] | | | |
| − | 0.639(47.7)[e] | 0.855(63.8)[e] | 0.532(39.7)[e] | 0.671(50.1)[e] |
| − + | 0.639(47.7)[e] | 0.767(57.2)[e] | | |

(a) Values for $\mu$mol-lecithin/$m^2$-Nucleosil were calculated from elemental analysis of carbon content using 50 mg of Nucleosil-300(7MI$_2$) particles derivatized with lecithin.

(b) Nucleosil-300(7MI$_2$) was stirred with lecithin imidazolide in a dry scintillation vial using dry CHCl$_3$ as solvent.

(c) An HPLC column containing Nucleosil-300(7MI$_2$) or Nucleosil- Lecithin from a previous coupling was perfused for 12-18 hours at 1.5 ml/min using about 7 mg/ml lecithin-imidazolide in dry CHCl$_3$. See methods.

(d) Nucleosil-300(7MI$_2$) particles were degassed by rotoevaporation after suspending the particles in dry CHCl$_3$. Care should be taken to avoid evaporation to dryness. (+) degas all reactions, (−) the degas step was omitted from every reaction, (− +) the first reaction was not degassed but the second reaction was degassed.

(e) The value in parenthesis reflects the mg-lecithin per gram of Nucleosil-lecithin. ——

UNITED STATES PATENT AND TRADEMARK OFFICE
CERTIFICATE OF CORRECTION

PATENT NO. : 4,931,498
DATED : June 5, 1990
INVENTOR(S) : Pidgeon

Page 3 of 3

It is certified that error appears in the above-identified patent and that said Letters Patent is hereby corrected as shown below:

In column 19, line 35, after "bonded", insert --.--, and delete "all reactions, (-) the degas step was omitted from every reaction, (- +) the first reaction was not degassed but the second reaction was degassed. (e)The value in parenthesis reflects the mg-lecithin per gram of Nucleosil-lecithin."

In column 22, line 6, replace "58" with --1--.

In column 23, line 28, replace "ab-" with --ad- --.

In column 26, line 3, replace "46" with --45--.

In column 26, line 28, replace "47" with --49--.

In column 26, line 29, replace "polypeptides" with --polypeptide--.

In column 26, line 31, replace "47" with --49--.

Signed and Sealed this

Eleventh Day of February, 1992

Attest:

HARRY F. MANBECK, JR.

*Attesting Officer*  *Commissioner of Patents and Trademarks*